(12) United States Patent
Ogundiwin et al.

(10) Patent No.: US 10,334,797 B2
(45) Date of Patent: Jul. 2, 2019

(54) MELON PLANTS WITH A DOMINANT MELON YELLOWING ASSOCIATED VIRUS (MYAV) RESISTANCE GENE

(71) Applicant: NUNHEMS B.V., Nunhem (NL)

(72) Inventors: Ebenezer Ogundiwin, Woodland, CA (US); Dyeme Bento, Rio Grande do Norte (BR); Peter Visser, Gainesville, FL (US)

(73) Assignee: NUNHEMS B.V., Nunhem (NL)

( * ) Notice: Subject to any disclaimer, the term of this patent is extended or adjusted under 35 U.S.C. 154(b) by 72 days.

(21) Appl. No.: 15/316,456

(22) PCT Filed: Jun. 1, 2015

(86) PCT No.: PCT/EP2015/062071
§ 371 (c)(1),
(2) Date: Dec. 5, 2016

(87) PCT Pub. No.: WO2015/185475
PCT Pub. Date: Dec. 10, 2015

(65) Prior Publication Data
US 2018/0146633 A1    May 31, 2018

Related U.S. Application Data

(60) Provisional application No. 62/008,691, filed on Jun. 6, 2014.

(51) Int. Cl.
| | | |
|---|---|---|
| *A01H 1/04* | (2006.01) | |
| *A01H 5/08* | (2018.01) | |
| *C12Q 1/6827* | (2018.01) | |
| *C12Q 1/6895* | (2018.01) | |
| *A01H 1/02* | (2006.01) | |
| *G01N 33/02* | (2006.01) | |

(52) U.S. Cl.
CPC ............. *A01H 1/04* (2013.01); *A01H 1/02* (2013.01); *A01H 5/08* (2013.01); *C12Q 1/6827* (2013.01); *C12Q 1/6895* (2013.01); *G01N 33/025* (2013.01)

(58) Field of Classification Search
None
See application file for complete search history.

(56) References Cited

U.S. PATENT DOCUMENTS 10,034,441 B2   7/2018   Ogundiwin et al.
2009/0013435 A1   1/2009   Hofstede et al.

FOREIGN PATENT DOCUMENTS

| EP | 1962578 B1 | 5/2011 |
|---|---|---|
| WO | WO 2007/073167 A1 | 6/2007 |
| WO | WO 2014/090968 A1 | 6/2014 |

OTHER PUBLICATIONS

Allen et al., Transcript-specific, single-nucleotide polymorphism discovery and linkage analysis in hexaploid bread wheat (*Triticum aestivum* L.), Plant Biotechnology J., 2011, vol. 9, pp. 1086-1099.
Ávila et al., "Produção do anti-soro e detecção por DAS-Elisa do Melon yellowing-associated virus em meloeiro", Trop. Plant Pathol., vol. 33 No. 3, Brasilla maio/Jun. 2008, pp. 245-247.
Boissot et al., "Mapping and Validation of QTLs for Resistance to Aphids and Whiteflies in Melon", Theoretical and Applied Genetics, 2010, vol. 121:1, pp. 9-20.
Cuevas et al., A consensus Linkage Map Identifies Genomic Regions Controlling Fruit Maturity and Beta-carotene-asso. Flesh Color in Melon Theoretical and Applied Genetics, 2009, vol. 119:4, pp. 741-756.
Eduardo et al., "Estimating the Genetic Architecture of Fruit Quality Traits in Melon Using a Genomic Library of Near Isogenic Lines", Journal of the American Society for Horticultural Science, 2007, vol. 132:1, pp. 80-89.
Garcia-Mas et al., The genome of melon (*Cucumis melo* L.), PNAS Jul. 17, 2012, vol. 109, No. 29, pp. 11872-11877.
Gonzales et al., "Generation of a BAC-based physical map of the melon genome", BMC Genomics, 2010, vol. 11, No. 339, pp. 1-13.
Henikoff et al., "Amino acid substitution matrices from protein blocks", PNAS 1992, vol. 89, pp. 10915-10919.
International Search Report and Written Opinion issued in International Patent Application No. PCT/EP2015/062071 dated Aug. 5, 2015.
Ji et al. "Ty-3, a begomovirus resistance locus near the Tomato yellow leaf curl virus resistance locus Ty-1 on chromosome 6 of tomato", Mol. Breeding 2007, vol. 20, pp. 271-284.
Lima et al., "Deteção por sorologia do Melon yellowing associated virus (MYaV) em áreas produtoras de melão no Nordeste brasileiro", Hortic. Bras. vol. 27 No. 4, Brasilla Oct./Dec. 2009, pp. 478-483.
Nagata et al. "Analysis of the triple gene block sequence in an important melon pathogen, Melon yellowing-associated virus", J Gen Plant Pathol, 2010, vol. 76, pp. 268-272.
Nagata et al., "A novel melon flexivirus transmitted by whitefly", Arch. Virology, 2005, vol. 150, pp. 379-387.
Nagata et al., "Isolation of a novel carlavirus from melon in Brazil", Plant Pathology, 2003, vol. 52, pp. 797.
Nuez et al., "Genetics of Melon yellows virus resistance derived from *Cucumis melo* ssp. *agrestis*", European Journal of Plant Pathology, 1999, vol. 105, pp. 453-464.
Okuda et al., "Resistance in melon to Cucurbit chlorotic yellow virus, a whitefly-transmitted crinivirus", Eur. J Plant Phathol, 2013, vol. 135, pp. 313-321.
Sebastian et al., "Cucumber (*Cucumis sativus*) and melon (*C. melo*) have numerous wild relatives in Asia and Australia, and the sister species of melon is from Australia", PNAS, 2010, vol. 107, No. 32, 14269-14273.
Verlaan et al., "Chromosomal rearrangements between tomato and Solanum chilense hamper mapping and breeding of the TYLCV resistance gene Ty-1", Plant Journal, 2011, vol. 68, pp. 1093-1103.

*Primary Examiner* — Brent T Page
(74) *Attorney, Agent, or Firm* — Arent Fox LLP

(57) ABSTRACT

The present invention relates to the field of melon plants having a dominant Melon Yellowing associated Virus (MYaV) resistance gene in their genome, introgressed from wild melon accessions.

16 Claims, 2 Drawing Sheets
Specification includes a Sequence Listing.

SEQUENCE LISTING

```
<160> NUMBER OF SEQ ID NOS: 30

<210> SEQ ID NO 1
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME15090

<400> SEQUENCE: 1
cattatgata tctttctctc aactcaacca tgaactctaa agcaccattc ccatctttca      60
tctttcggta cgctcgcaag gctgtagagt aggatacggg agacagagtt aggcctttct     120
tcggcatctc ttcaagaatg c                                               141

<210> SEQ ID NO 2
```

```
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME40332

<400> SEQUENCE: 2
ttgctgcaaa gccaccaact ccaggaattg ttagcagagg aattgctttg gagggtttct    60
gtagtatctt ggctggactc tggggtacag gtgccggatc aactacttta acggaaaatg   120
tacatactat tcatgtaaca a                                             141

<210> SEQ ID NO 3
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: mME12135

<400> SEQUENCE: 3
tgccagccgc acgtttcatc ttttggtaat aactattaaa agcataggaa gcatgtgctt    60
gaagggagtt aggatcgtaa caagcgccac cctgttgaat ggaacggcaa tcagcctgtc   120
cttcaccaca agcatagtcc a                                             141

<210> SEQ ID NO 4
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME28908

<400> SEQUENCE: 4
tccaatgtca tattttgatc cgcagcattt gccttcatct ggttgagttt agaataacaa    60
acgtcagtat taaattacaa caaaccagck atattaccaa aaagaaaaca atcaatcaga   120
taaggaaaac ctgaktggat t                                             141

<210> SEQ ID NO 5
<211> LENGTH: 139
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME36531

<400> SEQUENCE: 5
ctgttgaaat atattatgcc gttattttct tggaatattt gctgtcaaat cctgtgttat    60
tgactggtct tttttgttag gtctacgctg aaggaccagc tcgtcctact ggtggggctg   120
catgtacgcc gtctagact                                                139

<210> SEQ ID NO 6
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME9692
```

-continued

<400> SEQUENCE: 6
aagcacccct gtcattattt tgcataatct cacaaagtcc cccatcaaca gaaccttctt    60
caacattgtc atcctcgcct atatcatcat ctraaccaga cacttccttc tccaactgag   120
gattgtaygt ccattccaat c                                              141

<210> SEQ ID NO 7
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME50656

<400> SEQUENCE: 7 aaaagggaa gcaaaaagtt tcgaaggaat cgcatgtttc tgaagctctt gataagctca    60
gagagcagac cagagaggcg gttaagggc ttgaatcagt gtcaggtcct aaacctggtg   120
ttgatgaatt tggtaaagat g                                              141

<210> SEQ ID NO 8
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME21377

<400> SEQUENCE: 8
tgtatcagga acatagccag ctgctttcat cttctctggc aacgcctcca agaacatgta    60
gatttccttg acttgagggt gagatgtatc gccaccgaga acatatgtg ctttgccatt   120 tatctcgatc caactgcaac c                                              141

<210> SEQ ID NO 9
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME15090

<400> SEQUENCE: 9
cattatgata tctttctctc aactcaacca tgaactctaa agcaccattc ccatctttca    60
tctttcggta cgctcgcaag gctgtagagt aggatacggg agacagagtt aggcctttct   120
tcggcatctc ttcaagaatg c                                              141

<210> SEQ ID NO 10
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME12135

<400> SEQUENCE: 10
tgccagccgc acgtttcatc ttttggtaat aactattaaa agcataggaa gcatgtgctt    60
gaagggagtt aggatcgtaa caagcgccac cctgttgaat ggaacggcaa tcagcctgtc   120
cttcaccaca agcatagtcc a                                              141

<210> SEQ ID NO 11
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME36533

<400> SEQUENCE: 11
ctataatact tcaataaata acatgcatac atacatacat ggataatata gagagaagac    60
aaggatagct taagtttagt agttttgaag atgtgaatct cgattttat ctactacact    120 gtttgaatgg aatcctttc t                                              141

<210> SEQ ID NO 12
<211> LENGTH: 141
<212> TYPE: DNA
<213> ORGANISM: Cucumis melo
<220> FEATURE:
<221> NAME/KEY: variation
<222> LOCATION: (71)..(71)
<223> OTHER INFORMATION: SNP mME13585

<400> SEQUENCE: 12
catattattc ttaaataata taaaccacat aattattaaa ttaaattgaa ctaaaactac    60
cctattttaa tgctttacaa actcttatct aatgtatgct tcatttaatt attttttgg    120 ttgatacttt cattttattt t                                             141

<210> SEQ ID NO 13
<211> LENGTH: 42
<212> TYPE: DNA
<213> ORGANISM: Artificial Sequence
<220> FEATURE:
<223> OTHER INFORMATION: mME12135 primer - allele FAM(dye)

<400> SEQUENCE: 13
gaaggtgacc aagttcatgc tggtggcgct tgttacgatc ct                      42

<210> SEQ ID NO 14
<211> LENGTH: 42
<212> TYPE: DNA
<213> ORGANISM: Artificial Sequence
<220> FEATURE:
<223> OTHER INFORMATION: mME12135 pprimer -allele VIC(dye)

<400> SEQUENCE: 14
gaaggtcgga gtcaacggat tggtggcgct tgttacgatc cc                      42

<210> SEQ ID NO 15
<211> LENGTH: 25
<212> TYPE: DNA
<213> ORGANISM: Artificial Sequence
<220> FEATURE:
<223> OTHER INFORMATION: mME12135 Primer Common

<400> SEQUENCE: 15
aggaagcatg tgcttgaagg gagtt                                         25

<210> SEQ ID NO 16
<211> LENGTH: 47
<212> TYPE: DNA
<213> ORGANISM: artificial sequence
<220> FEATURE:
<223> OTHER INFORMATION: mME36531 - Primer allele FAM(dye)

<400> SEQUENCE: 16
gaaggtgacc aagttcatgc tcaaatcctg tgttattgac tggtctc            47

<210> SEQ ID NO 17
<211> LENGTH: 47
<212> TYPE: DNA
<213> ORGANISM: Artificial Sequence
<220> FEATURE:
<223> OTHER INFORMATION: mME36531 Primer allele VIC(dye)

<400> SEQUENCE: 17
gaaggtcgga gtcaacggat tcaaatcctg tgttattgac tggtctt            47

<210> SEQ ID NO 18
<211> LENGTH: 25
<212> TYPE: DNA
<213> ORGANISM: Artificial Sequence
<220> FEATURE:
<223> OTHER INFORMATION: mME36531 Primer Common

<400> SEQUENCE: 18
ggtccttcag cgtagaccta acaaa                                    25

<210> SEQ ID NO 19
<211> LENGTH: 44
<212> TYPE: DNA
<213> ORGANISM: Artificial Sequence
<220> FEATURE:
<223> OTHER INFORMATION: mME21377 Primer allele FAM(dye)

<400> SEQUENCE: 19
gaaggtgacc aagttcatgc tggcgataca tctcaccctc aagt               44

<210> SEQ ID NO 20
<211> LENGTH: 43
<212> TYPE: DNA
<213> ORGANISM: Artificial Sequence
<220> FEATURE:
<223> OTHER INFORMATION: mME21377 Primer allele VIC(dye)

<400> SEQUENCE: 20
gaaggtcgga gtcaacggat tgcgatacat ctcaccctca agc                43

<210> SEQ ID NO 21
<211> LENGTH: 25
<212> TYPE: DNA
<213> ORGANISM: Artificial Sequence
<220> FEATURE:
<223> OTHER INFORMATION: mME21377 Primer Common

<400> SEQUENCE: 21
gcaacgcctc caagaacatg tagat                                    25

<210> SEQ ID NO 22
<211> LENGTH: 41
<212> TYPE: DNA
<213> ORGANISM: Artificial Sequence
<220> FEATURE:
<223> OTHER INFORMATION: mME15090 Primer allele FAM(dye)

<400> SEQUENCE: 22
gaaggtgacc aagttcatgc tactctacag ccttgcgagc t                  41

<210> SEQ ID NO 23
<211> LENGTH: 41
<212> TYPE: DNA
<213> ORGANISM: Artificial Sequence
<220> FEATURE:
<223> OTHER INFORMATION: mME15090 Primer allele VIC(dye)

<400> SEQUENCE: 23
gaaggtcgga gtcaacggat tactctacag ccttgcgagc g         41

<210> SEQ ID NO 24
<211> LENGTH: 29
<212> TYPE: DNA
<213> ORGANISM: Artificial Sequence
<220> FEATURE:
<223> OTHER INFORMATION: mME15090 Primer Common

<400> SEQUENCE: 24
ctaaagcacc attcccatct ttcatcttt                       29

<210> SEQ ID NO 25
<211> LENGTH: 51
<212> TYPE: DNA
<213> ORGANISM: Artificial Sequence
<220> FEATURE:
<223> OTHER INFORMATION: mME36533 Primer alllel FAM(dye)

<400> SEQUENCE: 25
gaaggtgacc aagttcatgc tagattcaca tcttcaaaac tactaaactt c    51

<210> SEQ ID NO 26
<211> LENGTH: 52
<212> TYPE: DNA
<213> ORGANISM: Artificial Sequence
<220> FEATURE:
<223> OTHER INFORMATION: mME36533 Primer allele VIC(dye)

<400> SEQUENCE: 26
gaaggtcgga gtcaacggat tgagattcac atcttcaaaa ctactaaact ta    52

<210> SEQ ID NO 27
<211> LENGTH: 30
<212> TYPE: DNA
<213> ORGANISM: Artificial Sequence
<220> FEATURE:
<223> OTHER INFORMATION: mME36533 Primer Common

<400> SEQUENCE: 27
catggataat atagagagaa gacaaggata                      30

<210> SEQ ID NO 28
<211> LENGTH: 50
<212> TYPE: DNA
<213> ORGANISM: Artificial Sequence
<220> FEATURE:
<223> OTHER INFORMATION: mME13585 Primer allele FAM(dye)

<400> SEQUENCE: 28
gaaggtgacc aagttcatgc tgcatacatt agataagagt ttgtaaagcg    50

<210> SEQ ID NO 29
<211> LENGTH: 51
<212> TYPE: DNA
<213> ORGANISM: Artificial Sequence
<220> FEATURE:
<223> OTHER INFORMATION: mME13585 Primer allele VIC(dye)

```
<400> SEQUENCE: 29
gaaggtcgga gtcaacggat tagcatacat tagataagag tttgtaaagc a          51

<210> SEQ ID NO 30
<211> LENGTH: 30
<212> TYPE: DNA
<213> ORGANISM: Artificial Sequence
<220> FEATURE:
<223> OTHER INFORMATION: mME13585 Primer Common

<400> SEQUENCE: 30
ttaaattgaa ctaaaactac cctattttaa                                  30
```

MELON PLANTS WITH A DOMINANT MELON YELLOWING ASSOCIATED VIRUS (MYAV) RESISTANCE GENE

CROSS REFERENCE TO RELATED APPLICATIONS

This application is a 35 U.S.C. 371 National Phase of PCT Application No. PCT/EP2015/062071 dated Jun. 1, 2015, which claims benefit to U.S. provisional application No. 62/008,691 dated Jun. 6, 2014. The disclosure of these prior applications are hereby incorporated by reference in their entirety.

FIELD OF THE INVENTION

The present invention relates to the field of plant breeding, in particular melon breeding. The invention provides for the genetic locus conferring Melon Yellowing associated Virus (MYaV) resistance as found in wild melon accessions or in wild relatives of melon, and cultivated melon plants comprising said genetic locus (or a resistance conferring part thereof), which confers on said plants MYaV resistance. Also provided are seeds from which such plants can be grown, plant parts, cells, tissues or organs of such plants and breeding methods for transferring the MYaV resistance locus, or a resistance conferring part thereof, to other cultivated melon plants or plant cells, especially to MYaV susceptible melon plants. Also provided are molecular markers with which said genetic locus can be identified in plants and plant cells and/or transferred into other melon plants or plant cells. As the MYaV resistance present at the genetic locus is dominant, the MYaV resistant plants and/or plant cells may comprise the genetic locus in homozygous form or heterozygous form.

BACKGROUND OF THE INVENTION

Since 1999, a new disease which causes symptoms described as "yellowing of melon plants" was reported to cause damage in north-eastern Brazil, which is the region where more than 90% of the Brazilian melon production takes place. Symptoms are leaf mottling and yellowing and are mainly seen on older leaves (Nagata et al. 2003, Plant Pathology 52, 797). The virus causing this disease was tentatively named Melon yellowing-associated Virus (MYaV) (Nagata et al., 2003, supra and Nagata et al., 2005, Arch. Virology Vol. 150(2):379-87). In 2007 serological detection (using a polyclonal anti-bodies developed for MYaV detection, (see Avila et al. 2008 Trop. Plant Pathol. v. 33 n. 3 Brasilia maio/jun. 2008) revealed that a large percentage of symptomatic melon plants were indeed infected with MYaV (Lima et al. Hortic. Bras. vol. 27 no. 4 Brasilia October/December 2009). The worst affected region was in the state Rio Grande do Norte, in Mossoro, with 96.3% of melons being infected. Interestingly, virus concentrations were higher in extracts prepared from stems of symptomatic plants than from leaves.

Figure 1:
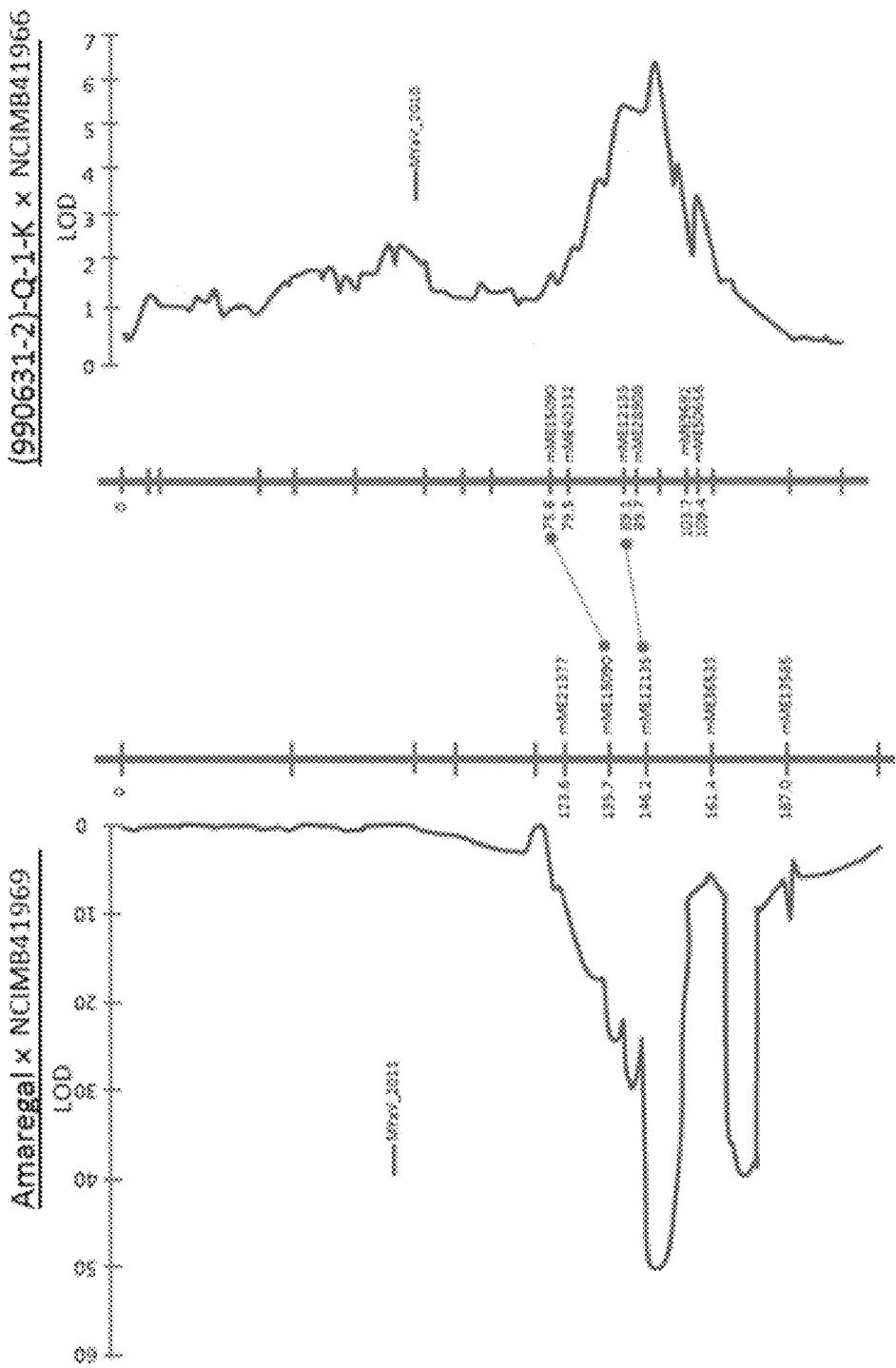
Figure 2:

The typical symptoms of the disease appear as leaf mottling and yellowing, mainly of older leaves, similar to a nutritional disorder (see Nagata et al, 2003, supra and FIG. 1 of Nagata et al. 2010, Journal of General Plant Pathology Volume 76, No. 4, page 268-272). In infected leaf tissue showing yellowing symptoms filamentous virus particles of 600-700 nm length can be seen by electron microscopy.

The virus found in plants with the yellowing disease symptoms is transmitted from melon to melon plants by whiteflies (*Bemisia tabaci* biotype B). Also grafting can be used to transmit the virus to other melon plants or to *Cucumis anguria* (West Indian gherkin). By electron microscopy, long, filamentous *Carlavirus*-type particles and inclusion bodies were seen in infected leaves, which suggested the presence of a virus of the genus *Carlavirus* (Nagata et al. 2003, Plant Pathol 52:797). Nagata et al. 2005 (supra) sequenced two genes, the coat protein (ORF-A) and one more open reading frame (ORF-B), see GenBank Accession number AY373028. As Cowpea mild mottle virus (CPMMV) was the only *carlavirus* species known to be transmitted by whiteflies, genetic and serological properties of MYaV were expected to be similar to CPMMV. However, MYaV did not cross-react in a dot-immunobinding assay to antibody of CPMMV (Nagata et al. 2003, supra), and genomic sequence data showed that the coat protein (CP) of CPMMV was not closely related to that of MYaV (Nagata et al. 2005, supra).

Initially it was unclear whether to include MYaV within the *Carlavirus* genus or if it should be a new genus in the family Flexiviridae (Nagata et al. 2005, supra). However, in a recent study (Nagata et al. 2010, supra), an estimated 40% (ca. 3.1 kb) of the MYaV genome was cloned and sequenced and based on these data the authors suggest that the virus is indeed a new species within the genus *Carlavirus* and they suggest to change the name of this virus to Mellon Yellowing Virus (MYV). The 3.1 kb sequence contained 5 open reading frames (ORFs), encoding three Triple Gene Block proteins (TGB1, TGB2 and TGB3), the coat protein (CP) and putative nucleic acid binding protein (NABP), see GenBank Accession number AB510477. The coat protein (CP) sequence in this study had 93% sequence identity to the sequence of ORF-A (AY373028).

As no plants with resistance against the virus are available, one strategy developed to limit MYaV infection is to cover the whole field with spunbond nonwoven fabric layer from germination until flowering, to prevent whitefly transmission of the virus. However, plants became sensitive to leaf miners (*Liriomisa* spp.), which became widespread and heavily damaged fruit production (Nagata et al. 2010, supra).

It is an object of the invention to provide MYaV resistance sources and a genetic region comprising the resistance locus or a part thereof, which confer resistance against MYaV. It is a further object of the invention to provide cultivated melon plants (*Cucumis melo* L.) and cells, tissues, fruits and other parts of such plants comprising in their genome a MYaV resistance-conferring locus (or a resistance-conferring part thereof), either in homozygous or heterozygous form, whereby the melon plants are resistant against MYaV. Also seeds from which MYaV resistant melon plants can be grown are an embodiment of the invention.

In a further aspect molecular markers are provided, which can be used to detect the presence of and/or to transfer the MYaV resistance-conferring locus, or a resistance-conferring part thereof, in/into plants or plant cells of *Cucumis melo* L. One or more of the markers can, thus, for example be used to transfer the resistance locus, or a resistance-conferring part thereof, into melon plants which are susceptible to MYaV. In one embodiment the resistance locus, or resistance-conferring part thereof, is the locus on chromosome 6 as found in seeds deposited under accession number NCIMB 41966 or NCIMB 41969. In another embodiment the resistance locus, or resistance-conferring part thereof, is the locus on chromosome 6 as found in seeds deposited under accession number NCIMB41967 (Local 2) or NCIMB41968 (*Papaya* Netted). In a further embodiment the resistance locus or resistance-conferring part thereof is the locus on chromosome 6, or a resistance-conferring part thereof, as found in other wild melon plants or wild relatives of melon.

One or more of the markers linked to, or associated with, the MYaV resistance locus, or resistance conferring part thereof, can also be used to identify new MYaV-resistance sources, such as other wild accessions of *Cucumis melo* or wild relatives of melon comprising an MYaV-resistance locus on chromosome 6 and for transferring (introgressing) the resistance locus, or a MYaV-resistance conferring part thereof, from such accessions into cultivated melon plants. The MYaV resistance conferring quantitative trait locus (QTL) on chromosome 6 (equivalent to ICuGI Linkage Group VI, or LG VI) was named MYaV6.1.

EP1962578B1 describes a CYSDV (Cucurbit Yellow Stunting Disorder Virus) resistance QTL of PI313970 on a linkage group which is therein arbitrarily designated as "LG6" and claims melon plants comprising an introgression from PI313970, which introgression comprises a CYSDV resistance QTL linked to at least one marker located on the chromosome equivalent to linkage group (LG) 6 of melon accession PI313970. It is noted that the in EP1962578B1 arbitrarily named LG6 corresponds to ICuGI Linkage Group V (LG V). In one aspect the plant of the invention i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo*, does not comprise the CYSDV resistance QTL as described in EP1962578B1. In another aspect the plant of the invention i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo* does not comprise the marker E11/M49-239 as defined in paragraph [0037] and claim 1 of EP 1962578 B1. In yet another aspect the plant of the invention does not comprise one or more or all of the markers E11/M54-156, E14/M54-152, E14/M51-210, E14/M51-083, E11/M49-239, E11/M54-169, E14/M50-262, E11/M57-278, E11/M54-163 and/or E11/M49-072 as defined in paragraph [0040] of EP1962578 B1. In still another embodiment the plant of the invention does not comprise one or more or all of the markers E11/M54-156, E14/M54-152, E14/M51-210, E14/M51-083, E11/M49-239, E11/M64-169, E14/M60-262, E11/M67-278, E11/M64-163 and/or E11/M49-072 as defined in paragraph [0013] of EP 1962578 B1 or as shown in FIG. 1. The cited passages of EP1962578B1 are enclosed herein by reference. In still another aspect the plants of the invention, i.e. a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild plant of the species *Cucumis melo*, does not have a CYSDV resistance phenotype (i.e. is not resistant to CYSDV as described in EP 1962578B1).

GENERAL DEFINITIONS

The indefinite article "a" or "an" does not exclude the possibility that more than one of the element is present, unless the context clearly requires that there be one and only one of the elements. The indefinite article "a" or "an" thus usually means "at least one".

As used herein, the term "plant" includes the whole plant or any parts or derivatives thereof, such as plant organs (e.g., harvested or non-harvested storage organs, tubers, fruits, leaves, seeds, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested melon fruits or parts thereof), flowers, leaves, seeds, tubers, bulbs, clonally propagated plants, roots, rootstocks, stems, root tips and the like. Also any developmental stage is included, such as seedlings, immature and mature, etc. When "seeds of a plant" are referred to, these either refer to seeds from which the plant can be grown or to seeds produced on the plant, after self-fertilization or cross-fertilization.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Thus, for example reference may herein be made to a MYaV-allele of the MYaV resistance locus MYaV6.1.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a gene or genetic marker is found. The MYaV resistance locus (or MYaV resistance-conferring locus) is, thus, the location in the genome of melon, where the MYaV-resistance gene is found. In cultivated melon the MYaV resistance locus is found on chromosome 6 (using the ICuGI nomenclature for chromosome or Linkage Groups, i.e. LG VI) and is preferably introgressed into the cultivated melon genome (i.e. onto chromosome 6, or LG VI) from wild melon accessions, such as (but not limited to) the wild melon accessions deposited under accession numbers NCIMB 41966 and NCIMB41969 and NCIMB41967 and NCIMB41968, or from other wild melons or wild relatives of melon which are crossable with *C. melo* and from which crosses fertile offspring can be produced.

A "quantitative trait locus", or "QTL" is a chromosomal locus that encodes for one or more alleles that affect the expressivity of a continuously distributed (quantitative) phenotype. The MYaV resistance conferring quantitative trait locus is named herein MYaV6.1.

"ICuGI" refers to the International Cucurbit Genomics Initiative, which publishes genetic maps of e.g. *Cucumis melo* (http://www.icugi.org/cgi-bin/cmap/map_set_info?species_acc=CM). The current version of the *C. melo* genome map is of Mar. 4, 2012 and the map of chromosome 6 is referred to as ICuGI_VI (or LG VI, or Linkage Group VI) and contains 124 markers (11 AFLP, 1 ISSR, 19 RAPD, 17 RFLP, 31 SNP, 45 SSR markers) on a linkage group spanning 0.00 to 98.00 cM. Herein melon chromosome 6 and LG VI are used interchangeably.

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Physical distance" between loci (e.g. between molecular markers and/or between phenotypic markers) on the same chromosome is the actually physical distance expressed in base pairs (bp), kilo base pairs (kb) or megabase pairs (Mb). *C. melo* has a total haploid genome size of about 450 Mb, divided into 12 chromosome pairs, see Garcia-Mas et al, PNAS Jul. 2, 2012, p 1-6 and Gonzales et al. 2010, BMC Genomics 11:339, p 1-13.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In melon, wild melon accessions or wild relatives of melon are often used to introgress fragments of the wild genome into the genome of cultivated melon, *Cucumis melo*. Such a cultivated melon plant thus has a "genome of cultivated *C. melo*", but comprises in the genome a fragment of a wild melon or of a wild relative of melon, e.g. an introgression fragment of a related wild *Cucumis* genome, such as *Cucumis melo* ssp. *agrestis, C. melo* ssp. *melo, C. melo* ssp. *acidulous, C. callosus, C. trigonus, C. picrocarpus*, or another wild melon or wild relative of melon. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

The "MYaV-allele" refers to a MYaV resistance-conferring allele found at the MYaV resistance-conferring locus MYaV6.1, or at the resistance-conferring part of the locus, introgressed into cultivated melon (onto cultivated *C. melo* chromosome 6) from a wild melon or wild relative of melon, e.g. from plants of which a representative sample of seeds were deposited under accession number NCIMB 41966 or NCIMB 41969 or NCIMB41967 or NCIMB41968. The term "MYaV-allele", thus, also encompasses MYaV-alleles obtainable from other MYaV resistant *Cucumis* accessions, such as MYaV orthologous alleles (see below). When one or two MYaV-alleles are present at the MYaV resistance-conferring locus in the genome (i.e. in heterozygous or homozygous form), the plant is resistant against MYaV, i.e. has a MYaV resistance phenotype. In cultivated melon plant lacking the introgression fragment, the *C. melo* allele found at the same locus on chromosome 6 is herein referred to as "myav" allele (or MYaV-susceptible allele). As the resistance is dominant, myav/myav plants show a MYaV-susceptible phenotype, whereas MYaV/myav plants and MYaV/MYaV plants are plants which possess the MYaV resistant phenotype conferred by the MYaV-allele (i.e. are resistant to MYaV).

"MYaV orthologous alleles" or "MYaV orthologs" or "orthologs of MYaV" are alleles of MYaV resistance genes present in other wild melon or wild relatives of melon, on the orthologous chromosomes 6. Such orthologous alleles may, thus, be found on orthologous chromosome 6 of wild melon or wild relatives of *C. melo*, (such as *C. callosus, C. trigonus, C. picrocarpus* and others) and are transferrable, by introgression, onto cultivated *C. melo* chromosome 6. Thus an "orthologous" allele (also referred to as "variant allele") refers to an allele, or an introgression fragment comprising the allele, which is derived from different wild melons or wild relative of melon plant than the one present in any of the seed deposits made herein, but which variant comprises one or more of the SNPs linked to the QTL (resistant SNP genotype) and wherein the variant genomic sequence comprises substantial sequence identity to the SEQ ID NO: comprising the SNP (any one of SEQ ID NO: 1, 2, 3, 4, 6, 7, 8, 9, 10, 11 or 12), i.e. at least 85%, 90%, 95%, 98%, 99% sequence identity or more. Thus, when reference herein is made to a resistant SNP genotype in a specific genomic sequence (selected from SEQ ID NO: 1, 2, 3, 4, 6, 7, 8, 9, 10, 11 or 12), this encompasses also the resistant SNP genotype in variants of the genomic sequence, i.e. the SNP genotype in a genomic sequence comprising at least 85%, 90%, 95%, 98%, 99% sequence identity or more to the sequence referred to (selected from SEQ ID NO: 1, 2, 3, 4, 6, 7, 8, 9, 10, 11 or 12). Thus any reference herein to any one of SEQ ID NO: 1, 2, 3, 4, 6, 7, 8, 9, 10, 11 or 12 in one aspect also encompasses a variant of any one of SEQ ID NO: 1, 2, 3, 4, 6, 7, 8, 9, 10, 11 or 12, said variant comprising at least 85%, 90%, 95%, 98%, 99% sequence identity or more to said sequence and comprising the resistant SNP genotype.

"Uniformity" or "uniform" relates to the genetic and phenotypic characteristics of a plant line or variety. Inbred lines are genetically highly uniform as they are produced by several generations of inbreeding. Likewise, and the F1 hybrids which are produced from such inbred lines are highly uniform in their genotypic and phenotypic characteristics and performance.

A genetic element, an introgression fragment or a gene or allele conferring a trait (such as resistance against MYaV) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

A "MYaV resistance phenotype" or "MYaV resistance" or "MYaV resistant plants" refers to resistance against MYaV conferred by the MYaV allele (or by the MaYV orthologous allele) when present in the *C. melo* genome in two copies (in homozygous form) or in one copy (in heterozygous form). The MYaV resistance phenotype and the presence of the MYaV allele and/or orthologs of MYaV can be tested using the "MYaV resistance assay" and/or the MYaV marker assays. In one aspect the term "MYaV resistance" encompasses additionally, or alternatively, resistance against a yellowing virus transmitted by *Bemisia tabaci* biotype B, present in the same locations as MYaV (e.g. north-eastern Brazil), which results in the same or essentially similar symptoms as MYaV infection, and against which the MYaV allele (or by the MaYV orthologous allele) of the invention confers resistance when present in the *C. melo* genome in two copies (in homozygous form) or in one copy (in heterozygous form). This yellowing virus resistance phenotype and/or the presence of the MYaV allele and/or orthologs of MYaV can be tested using the "MYaV resistance assay" and/or the MYaV marker assays as described.

A "MYaV resistance assay" can be carried out in different ways, either by grafting or, preferably, as a field test, as also described elsewhere herein. Preferably a field assay is used in an area of natural high incidence of *Bemisia tabaci* biotype B carrying MYaV, such as north-eastern Brazil, or other areas where a high disease incidence of MYaV is present (i.e. an MYaV infested area). A plant of a particular genotype is considered to be MYaV-resistant if the average disease-resistance score of a plurality of plants (at least 4, 5, 6, 7, 8, 9, 10 or more, in preferably at least two or three replicates) of that genotype is significantly higher compared to the susceptible controls (plants lacking an introgression fragment which comprises an MYaV-allele or an MYaV-ortholog, such as Galia melon varieties Amaregal F1 (Nunhems) or Glory (Origene Seeds); or Piel de Sapo melon varieties Medellin (Nunhems) or Sancho (Syngenta)), when grown in the same environment. Thus, for example, melon plants of a line comprising the introgression of the MYaV-resistance conferring locus, or a resistance conferring part thereof, in heterozygous or homozygous form may be grown together with suitable control melon plants (especially MYaV-susceptible melon plants) in an open field in north-eastern Brazil and when all plants of susceptible controls show clear yellowing symptoms (see FIG. 2) all plants are phenotyped on a disease-resistance scale of 1 (totally yellow leaves, i.e. leaves in the first ⅓$^{rd}$ of the plant are 100% yellow) to 9 (totally green leaves; leaves in the first ⅓$^{rd}$ of the plant are 100% green), whereby 2=about 81% to 99% of leaf area in the first ⅓$^{rd}$ of the plant is yellow, 3=about 65% to 80% of leaf area in the first ⅓$^{rd}$ of the plant is yellow, 4=about 49% to 64% of leaf area in the first ⅓$^{rd}$ of the plant is yellow, 5=about 33% to 48% of leaf area in the first ⅓$^{rd}$ of the plant is yellow, 6=about 17% to 32% of leaf area in the first ⅓$^{rd}$ of the plant is yellow, 7=up to about 17% of leaf area in the first ⅓$^{rd}$ of the plant is yellow, 8=few leaves in the first ⅓$^{rd}$ of the plant start to show yellow shadow/mottling. The first ⅓$^{rd}$ of the plant refers to the older leaves in the first ⅓$^{rd}$ area of the plant as determined from the main stem/root system of the plant and as seen in FIG. 2 (black rectangle). The younger leaves on the vines, further towards the tip of the vines, are not phenotyped, as these are generally green at the moment of phenotyping and turn yellow only on susceptible plants after several more days, e.g. 7-10 days later (although they do already contain the virus at the moment of phenotyping). Plants with an average disease-resistance score that is significantly higher than the average disease score of the susceptible controls, e.g. an average score of at least 3.0, preferably at least 4.0, more preferably at least 5.0, at least 6.0, at least 7.0, at least 8.0, most preferably 9.0, are herein MYaV-resistant plants or plants having an MYaV resistance.

The "MYaV-marker assay" is a molecular marker assay which can be used to test whether on *C. melo* chromosome 6 an introgression from a wild melon, or wild relative of melon, comprising the MYaV-allele (or an orthologous allele) is present in the genome (or whether in wild melon or wild relatives of melon comprise the MYaV6.1 QTL-comprising region in their genome), by determining the genotype of any one or more markers linked to the QTL, e.g. the genotype of SNP markers mME15090 and/or mME12135 (in one aspect preferably both mME15090 and mME12135), and/or any wild melon or wild-relative of melon genome-specific marker in between SNP markers mME15090 and mME12135, and/or within 7 cM or within 5 cM of either of these markers, and/or within 5 Mb, 3 Mb, 2 Mb or 1 Mb or less of either of these markers, and/or optionally either A) of one or more markers selected from the group mME40332, mME28908, mME9692, mME50656, or any wild-*C. melo*-genome or wild melon relative genome-specific marker between mME1509 and mME50656, and/or B) of one or more markers selected from the group mME21377, mME36533, mME13585, or any wild *C. melo*-genome specific marker or wild melon relative genome-specific between mME21377 and mME13585 and/or C) of one or more markers selected from the group mME21377, mME13585, or any wild *C. melo*-genome specific marker or wild melon relative genome-specific between mME21377 and mME13585, especially between mME21377 and mME12135.

"Melon" or "muskmelon" refers herein to plants of the species *Cucumis melo*. Melons or 'muskmelons', *Cucumis melo*, can be classified into: *C. melo cantalupensis*, *C. melo inodorous* and *C. melo reticulatus*. *C. melo cantalupensis* are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. *C. melo inodorous* (or winter melons) can be subdivided into different types, such as Honeydew melon, Piel de Sapo, Sugar melon, Japanese melon, etc. *C. melo reticulatus* is the true muskmelon, with reticulated skin (netted) and includes Galia melons, Sharlyn melons and the North American cantaloupe.

"Cultivated melon" refers to plants of *Cucumis melo* i.e. varieties, breeding lines or cultivars of the species *C. melo*, cultivated by humans and having good agronomic characteristics, especially producing edible and marketable fruits of good size and quality and uniformity; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

Melon and the wild relatives of melon is/are diploid and has/have 12 pairs of homologous chromosomes, numbered 1 to 12. "Melon chromosome 6" refers to the *C. melo* chromosome 6, as known in the art and as referred to by the ICuGI nomenclature. "Orthologous chromosome 6" refers to the chromosome 6 of wild relatives of melon, parts of which can be introgressed into cultivated melon chromosome 6.

"Wild melon" includes wild plants of the species *Cucumis melo*, e.g. *C. melo* ssp *agrestis*, *C. melo* ssp. *melo*, *C. melo* var. *texanus*, *C. melo* var. *acidulous*, seeds deposited under NCIMB 41966, NCIMB 41969, NCIMB41962, NCIMB41968, and other wild *C. melo* accessions, as e.g. landraces or PI accessions found on http://www.ars-grin.gov or other seed collections. Seeds deposited under NCIMB 41966 were obtained from the ARS-GRIN collection in the USA and have as designated origin 'India'. Seeds deposited under NCIMB 41969 were obtained from Spain and have as origin Uzbekistan. Seeds deposited under accession number NCIMB 41967 and seeds deposited under NCIMB 41968 were obtained in the USA and have an unknown origin.

"Wild relatives of melon" include wild plants of other *Cucumis* species, but which can be crossed with *Cucumis melo* to produce fertile offspring (optionally with the aid of embryo rescue, temperature-dependent enhancement of pollen-tube growth, or similar techniques to overcome reproductive barriers) and from which chromosome fragments can be obtained and transferred into *Cucumis melo* (either by interspecific crosses with *C. melo* or via crosses with a bridge species). Examples of wild relatives of melon are *C. anguria*, *C. metuliferus*, *Cucumis callosus*, *Cucumis trigonus*, *Cucumis ficifolius*, *C. picocarpus*, *C. zeyheri*, *C. africanus*, *C. meeusei*, *C. prophetarum*, *C. hystrix*, *C. queenslandicus*, and other *Cucumis* species (see e.g. Sebastian et al. 2010, PNAS Vol 107, no. 32, 14269-14273).

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control show a statistically significant difference in that characteristic (e.g. $p<0.05$ using ANOVA) from the (mean of the) control.

A "recombinant chromosome" refers to a chromosome having a new genetic makeup arising through crossing over between homologous chromosomes, e.g. a "recombinant chromosome 6", i.e. a chromosome 6 which is not present in either of the parent plants and arose through a rare crossing-over event between homologous chromosomes of a chromosome 6 pair. Herein, for example, a recombinant melon chromosome 6 comprising a MYaV-resistance conferring locus, or resistance-conferring part thereof (comprising a MYaV-resistance allele), is provided.

The term "traditional breeding techniques" encompasses herein crossing, backcrossing, selfing, selection, double haploid production, embryo rescue, protoplast fusion, marker assisted selection, mutation breeding etc. as known to the breeder (i.e. methods other than genetic modification/transformation/transgenic methods), by which, for example, a recombinant chromosome 6 can be obtained, identified and/or transferred.

"Backcrossing" refers to a breeding method by which a (single) trait, such as MYaV resistance, can be transferred from an inferior genetic background (e.g. a wild melon or wild relative of melon; also referred to as "donor") into a superior genetic background (also referred to as "recurrent parent"), e.g. cultivated melon. An offspring of a cross (e.g. an F1 plant obtained by crossing a wild, MYaV-resistant melon with a cultivated, MYaV-susceptible melon; or an F2 plant or F3 plant, etc., obtained from selfing the F1) is "backcrossed" to the parent with the superior genetic background, e.g. to the cultivated, MYaV-susceptible, parent. After repeated backcrossing, the trait of the inferior genetic background will have been incorporated into the superior genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to an MYaV-resistance locus, can be used to detect and/or select melon plants comprising the MYaV-resistance locus. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g. within 7 cM or 5 cM, 4 cM, 3 cM, 2 cM, 1 cM or less) the less likely it is that the two markers will be separated from one another (and the more likely they will co-segregate as a unit).

A marker "within 7 cM or within 5 cM" of another marker refers to a marker which genetically maps to within the 7 cM or 5 cM region flanking the marker (i.e. either side of the marker) Similarly, a marker within 5 Mb, 3 Mb, 2 Mb, 1 Mb or less of another marker refers to a marker which is physically located within the 5 Mb, 3 Mb, 2 Mb or 1 Mb, or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage A LOD score of +3 indicates 1000 to 1 odds that the linkage being observed did not occur by chance.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Cell culture" or "tissue culture" refers to the in vitro culture of cells or tissues of a plant.

"Regeneration" refers to the development of a plant from cell culture or tissue culture or vegetative propagation.

"Transgene" or "chimeric gene" refers to a genetic locus comprising a DNA sequence, such as a recombinant gene or a recombinant chromosome or part thereof, which has been introduced into the genome of a melon plant by transformation, such as *Agrobacterium* mediated transformation. A plant comprising a transgene stably integrated into its genome is referred to as "transgenic plant". A transgene or transgenic plant may also contain a complete recombinant chromosome or part of a recombinant chromosome, e.g. the part comprising the MYaV-allele, introduced into the genome by transformation.

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and a gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Fine-mapping" refers to methods by which the position of a QTL can be determined more accurately (narrowed down) and by which the size of the introgression fragment comprising the QTL is reduced. For example Near Isogenic Lines for the QTL (QTL-NILs) can be made, which contain different, overlapping fragments of the introgression fragment within an otherwise uniform genetic background of the recurrent parent. Such lines can then be used to map on which fragment the QTL is located and to identify a line having a shorter introgression fragment comprising the QTL.

DETAILED DESCRIPTION OF THE INVENTION

The present invention relates to a cultivated *Cucumis melo* plant comprising resistance against Melon Yellowing associated Virus (MYaV). In particular, the resistance is conferred by an introgression fragment on melon chromosome 6, wherein said introgression fragment is from a wild plant of the species *Cucumis melo* or from a wild relative of melon.

The present inventors crossed two different wild *C. melo* accessions, representative seeds of which were deposited under NCIMB 41966 and NCIMB 41969, to a MYaV-susceptible melon breeding line and to a susceptible melon variety, respectively, and carried out QTL-mapping, based on phenotyping data obtained from MYaV-infested fields near Mossoro (Rio Grande do Norte, Brazil).

Surprisingly, in both mapping populations, a highly significant QTL for MYaV resistance was found on melon chromosome 6, indicating that different wild *Cucumis melo* accessions comprise a MYaV resistance locus on chromosome 6, which was transferred into cultivated *C. melo* and conferred MYaV-resistance onto the cultivated melon plant. In the two mapping populations the QTL, which was named MYaV6.1, explained 32.6% and 91.7% of the observed phenotypic variation for MYaV resistance, and is therefore highly significant.

It is noted that when reference herein is made to a (one) QTL (MYaV6.1) or to a MYaV resistance conferring locus (or a resistance conferring part thereof) on chromosome 6 of the *C. melo* genome, it can be that there are in fact two (or more) QTLs linked to each other on chromosome 6, as the LOD-score has two peaks in both mapping populations (see FIG. 1). So reference to one QTL or to one locus encompasses the possibility that there are two (or more) QTLs or two (or more) loci coupled to each other on chromosome 6. Equally reference herein to an introgression fragment on chromosome 6 having a QTL or an MYaV-resistance conferring locus (or resistance-conferring part thereof) encompasses that the introgression fragment comprises all resistance-conferring loci, or in cases of smaller introgression fragments, at least a large enough introgression region (with one, two or more QTLs) so that MYaV-resistance is conferred by the introgression fragment when the introgression fragment is in heterozygous or homozygous form in the *C. melo* genome. Thus, in case of smaller introgression fragments, the introgression fragment comprises preferably at least the major QTL (i.e. the larger of the two LOD-peaks in FIG. 1). In one aspect, the introgression fragment comprises the resistance genotype of at least one or both markers selected from the common markers mME15090 and mME12135. Especially the presence of the resistance genotype of marker mME12135 is indicative of the presence of the QTL. In one aspect the introgression fragment comprises the resistance genotype of at least one or both markers selected from the common markers mME15090 and mME12135 and/or any wild melon or wild-relative of melon genome-specific marker in between SNP markers mME15090 and mME12135, and/or within 7 cM or within 5 cM of either of these markers, and/or within 5 Mb, 3 Mb, 2 Mb or 1 Mb or less of either of these markers.

The two markers mME15090 and mME12135 were also found in two other wild accession, NCIMB 41967 and NCIMB 41968 and it was confirmed that these two wild *C. melo* accessions contain the QTL on chromosome 6. Both accessions were resistant against MYaV (with an average yellowing score of 9) and both accessions were crossed to susceptible melon cultivar Amaregal (a Galia melon) to produce, by backcrossing, a cultivated melon with an introgression fragment from NCIMB41967 or NCIMB41968 on chromosome 6. The QTL for MYaV resistance inherited as a monogenic dominant gene. Also the cultivated melons comprising the introgression on chromosome 6, as indicative by the presence of the resistance genotype of marker mME12135 and/or mME15090, were resistant against MYaV. See also the Examples.

Thus, in one aspect, it was found that a Quantitative Trait Loci (QTL MYaV6.1) which confers MYaV-resistance is present on chromosome 6 of wild melons and that this QTL, when transferred (introgressed) into a cultivated, MYaV-susceptible melon variety or breeding line, and when present in heterozygous or homozygous form, confers MYaV-resistance onto the cultivated melon plant. The QTL, or the introgression fragment comprising the QTL (comprising the MYaV-resistance allele), is thus dominant, i.e. it is sufficient to have the introgression fragment on one of the chromosomes 6 (one recombinant chromosome 6), while the homologous chromosome 6 of the pair may be a (non-recombinant) chromosome 6 of cultivated *C. melo* lacking the introgression fragment.

Although the present sources of MYaV-resistance allele introgressions are two wild sources (NCIMB 41966 and NCIMB 41969, from India and Uzbekistan, respectively), there are likely other wild *Cucumis* accessions which comprise MYaV-alleles or MYaV orthologous alleles at the same locus on chromosome 6. Such MYaV-alleles or MYaV-orthologous alleles can also be identified and introgressed into cultivated *C. melo* as described herein, to generate a cultivated *C. melo* plant comprising a genome of *C. melo* and a recombinant chromosome 6, whereby the recombinant chromosome 6 comprises a wild *Cucumis* species introgression fragment, which confers an MYaV-resistance phenotype onto the cultivated *C. melo* plant when present in homozygous or heterozygous form.

In one aspect, the inventors have found two additional wild accessions, NCIMB41967 and NCIMB41968, which comprise the QTL on chromosome 6 and which comprise the resistance genotype of marker mME12135 and/or mME15090, i.e. the genome of the plant comprises at least an A (genotype AA or AG) at nucleotide 71 of SEQ ID NO: 3 and/or at least a C (genotype CC or AC) at nucleotide 71 of SEQ ID NO: 1, respectively. These two wild accessions have also been used to make a cultivated melon (by backcrossing) comprising an MYaV-resistance phenotype conferred by an intregression fragment on chromosome 6 comprising the QTL from NCIMB41967 or NCIMB41968, as indicated by the presence of the resistance genotype of marker mME12135 and/or mME15090.

Other accessions of wild melons and wild relatives of melon, such as accessions obtainable from the USDA National Plant Germplasm System collection or other seed collections, can be screened for MYaV resistance using phenotypic and/or MYaV-marker assays, and resistant accessions can be crossed with a *Cucumis melo* plant lacking MYaV resistance. The F2 generation (or further generation, such as the F3 or a backcross generation) can then be screened for recombinant plants having the MYaV resistance phenotype and/or the introgression fragment or a part thereof, using the molecular marker assays described herein.

Plants, Seeds and Plant Parts According to the Invention

Thus, in a first embodiment a cultivated *Cucumis melo* plant comprising resistance against Melon Yellowing associated Virus (MYaV) is provided.

The presence of an MYaV resistance phenotype can be determined using the MYaV resistance assay, whereby plants are screened for resistance under natural field conditions in one or more areas where MYaV incidence is high, such as north-eastern Brazil. Plants according to the invention have MYaV resistance if their average disease score, on a scale of 9=totally green leaves (in the first ⅓rd of the plant) to 1=totally yellow leaves (in the first ⅓rd of the plant), is significantly higher than the average disease score of MYaV susceptible varieties, when grown under the same environmental conditions. The average disease score of MYaV resistant cultivated melon plants is, in one embodiment, at least 3, preferably at least 4, on a scale of 1=totally yellow leaves to 9=totally green leaves, when grown in the field in north-eastern Brazil, or in any other field where MYaV incidence is high. In another embodiment, the average disease score is at least 5, 6, 7, 8 or 9. Whether the MYaV incidence is high can be either seen due to the severe yellowing symptoms (average disease score=1) developing on the susceptible control plants, such as cultivars Sancho, Amaregal, or others. Alternatively or in addition MYaV virus levels can be determined in melon tissue, e.g. using polyclonal anti-bodies developed for MYaV detection.

Average disease scores are preferably calculated based on at least four plants of a line or variety, preferably at least 5, 10, 15, 20 or more plants grown under the same environmental conditions.

The resistance against MYaV is conferred by an introgression fragment on chromosome 6, wherein the introgression fragment is derived from a wild melon genome or from a wild relative of melon. The introgression fragment comprises the Quantitative trait locus (QTL) referred herein to as MYaV6.1, which locus in turn comprises a MYaV-resistance allele, or a MYaV-orthologous resistance allele, of the MYaV resistance gene.

The cultivated melon plants according to the invention, thus, have a recombinant chromosome 6, which comprises an introgression fragment of a wild melon chromosome 6 or of an orthologous chromosome 6 of a wild relative of melon.

As the resistance is dominant, the resistance phenotype is seen when the resistance allele (and the SNP linked to the allele) is in heterozygous or homozygous form, the cultivated melon plants according to the invention have the introgression fragment, or the resistance-conferring part thereof, on chromosome 6 in heterozygous or homozygous form.

In one aspect the introgression fragment is identifiable by at least one marker selected from:
a) the CC or AC genotype for the SNP marker mME15090 in SEQ ID NO: 1 (or SEQ ID NO: 9), or in a sequence comprising at least 85%, 90%, 95%, 98%, 99% sequence identity to SEQ ID NO:1 (or to SEQ ID NO: 9);
b) the AA or AG genotype for the SNP marker mME12135 in SEQ ID NO: 3 (or SEQ ID NO: 10) or in a sequence comprising at least 85%, 90%, 95%, 98%, 99% sequence identity to SEQ ID NO:3 (or to SEQ ID NO: 10).

In a further aspect the introgression fragment comprises the resistance genotype of at least one or both markers selected from the common markers mME15090 and mME12135 and/or any wild melon or wild-relative of melon genome-specific marker in between SNP markers mME15090 and mME12135, and/or within 7 cM or within 5 cM of either of these markers, and/or within 5 Mb, 3 Mb, 2 Mb or 1 Mb or less of either of these markers.

The introgression fragment is derivable from (or derived from) or obtainable from (or obtained from; or as present in) a wild plant of the species Cucumis melo, which comprises the MYaV QTL (MYaV6.1) on chromosome 6. Alternatively, the introgression fragment is derivable from (or derived from) or obtainable from (obtained from; or as present in) a wild relative of Cucumis melo, which can be crossed with Cucumis melo (optionally using embryo rescue or other techniques to aid production of viable offspring), so that the fragment of the orthologous chromosome 6 can be introgressed into the chromosome 6 of C. melo, especially cultivated C. melo.

In a specific embodiment, the introgression fragment comprising the MYaV resistance locus is derivable from (or derived from) or obtainable from (or obtained from; or as present in) wild C. melo plants, a representative sample of seeds of which has been deposited under accession number NCIMB 41966 or NCIMB41969 or NCIMB41967 or NCIMB 41968, or from other wild melon accessions or wild relatives of melon. In one embodiment the introgression fragment is identifiable by one or more of the markers described elsewhere herein, especially the presence of the resistance genotype of markers mME12135 and/or mME15090. In one aspect the introgression fragment is identifiable by the resistance genotype of at least one or both markers selected from the common markers mME15090 and mME12135 and/or any wild melon or wild-relative of melon genome-specific marker in between SNP markers mME15090 and mME12135, and/or within 7 cM or within 5 cM of either of these markers, and/or within 5 Mb, 3 Mb, 2 Mb or 1 Mb or less of either of these markers.

In one aspect the invention provides a cultivated C. melo plant which comprises resistance against MYaV, wherein the resistance is conferred by an introgression fragment on melon chromosome 6, wherein said introgression fragment (conferring said MYaV resistance) is obtained by (or obtainable by) crossing a wild C. melo plant which comprises one or more the markers disclosed herein (linked to the QTL; especially marker mME15090 and/or mME12135) and which comprises a MYaV-resistance phenotype with a cultivated melon plant.

In one embodiment the invention provides a cultivated C. melo plant which comprises resistance against MYaV, wherein the resistance is conferred by an introgression fragment on melon chromosome 6, wherein said introgression fragment (conferring said MYaV resistance) is obtained by (or obtainable by) crossing a plant of which seeds were deposited under accession number NCIMB 41966 or NCIMB41969 or NCIMB 41967 or NCIMB 41968 with a cultivated melon plant. These wild C. melo accessions have a MYaV-resistance phenotype, with an average disease score of 9.0 (leaves remain green), compared to an average disease score of below 2.0, or below 1.5, for the susceptible melon varieties, such as Amaregal F1. The introgression fragment may also be derived from (or obtained from) other wild C. melo plants or other wild relatives of melon, which have an average MYaV disease score of at least 7, preferably at least 8, more preferably 9, as e.g. determined in the MYaV resistance assay.

In another embodiment the invention relates to a plant of the invention i.e. a cultivated Cucumis melo plant comprising resistance against Melon Yellowing associated Virus (MYaV) wherein said resistance is conferred by an introgression fragment on chromosome 6 in homozygous or heterozygous form and wherein said introgression fragment is from a wild plant of the species Cucumis melo wherein the introgression fragment is in one aspect "as in"/is "identical to"/is "the same as in" the MYaV resistance conferring fragment on chromosome 6 as present in seeds deposited under number NCIMB 41967, NCIMB 41968, NCIMB 41966, NCIMB 41969, NCIMB 42113, or NCIMB 42198. As wild accessions will be genetically divergent, the genomic sequence of the introgression fragment will most likely not be identical, and even the resistance conferring gene (comprising a promoter, introns and exons) may be divergent in nucleotide sequence, but the function will be the same, i.e. conferring MYaV resistance. The divergence can also be seen herein, in that certain markers linked to the MYaV6.1 QTL are not 'common markers' (such as the common markers mME12135 and mME15090 which are found in all 4 accessions), but are specific for the MYaV6.1 QTL as found in a specific accession. So for example (in addition to the common markers) markers mME21377, mME36533 and/or mME13585 were found linked to the QTL in NCIMB41969; markers mME40332, mME28908, mME9692 and/or mME50656 were found linked to the QTL in accession NCIMB41966; markers mME21377 and/or mME13585 were found linked to the QTL in NCIMB41968 and NCIMB41967.

The skilled person is capable of identifying and introgressing the MYaV6.1 QTL comprising region found in other wild melon accessions or other wild relatives of melon into cultivated *C. melo* as will be explained further below. The skilled person is also able to identify other molecular markers linked to (associated with) the QTL, which can be used to identify the presence of an introgression fragment from such other wild melons or wild relatives of melon on chromosome 6 of *C. melo*. Two of the molecular markers provided herein were found to be associated with the MYaV-resistance QTL, where the introgression fragment was obtained from four different wild sources. These two markers may also be linked to (associated with) MYaV resistance on chromosome 6, or on orthologous chromosomes 6, and may thus be useful to derive the QTL from different sources. Alternatively, the skilled person can identify other molecular markers using known methods.

In one embodiment the presence of the introgression fragment, or the chromosome 6 region (or orthologous chromosome 6 region), comprising the MYaV resistance locus, is detectable by a molecular marker assay which detects at least one, preferably at least the following two Single Nucleotide Polymorphism (SNP) markers:

a) the CC or AC genotype for the SNP marker mME15090 in SEQ ID NO: 1 (or SEQ ID NO: 9) or in a sequence comprising at least 85%, 90%, 95%, 98%, 99% sequence identity to SEQ ID NO:1 (or to SEQ ID NO: 9);
b) the AA or AG genotype for the SNP marker mME12135 in SEQ ID NO: 3 (or SEQ ID NO: 10) or in a sequence comprising at least 85%, 90%, 95%, 98%, 99% sequence identity to SEQ ID NO:3 (or to SEQ ID NO: 10).

In another aspect the presence of the introgression fragment, or the chromosome 6 region (or orthologous chromosome 6 region), comprising the MYaV resistance locus, is detectable by a molecular marker assay which detects at least one, preferably at least two or more markers selected from the group consisting of: marker mME15090, marker mME12135, any wild melon or wild-relative of melon genome-specific marker in between SNP markers mME15090 and mME12135, any wild melon or wild-relative of melon genome-specific marker within 7 cM or within 5 cM of mME15090 or mME12135, any wild melon or wild-relative of melon genome-specific marker within 5 Mb, 3 Mb, 2 Mb or 1 Mb or less of mME15090 or mME12135.

As mentioned, the two SNP markers mME15090 and mME12135 were found to be genetically linked to (or associated with) the introgression fragment on chromosome 6 comprising the QTL MYaV6.1 in both mapping populations, i.e. in plants comprising the resistance QTL from two different wild melon accessions and also in two other wild melon accessions, namely NCIMB41967 and NCIMB41968 which were MYaV resistant. These two markers are referred to as common markers, as they were found to be linked to the QTL in four wild accessions.

Thus, in one embodiment the MYaV resistant plants according to the invention comprise at least a Cytosine (C) (i.e. the CC or AC genotype) instead of two Adenines (AA) at nucleotide 71 of SEQ ID NO:1 (or SEQ ID NO:9) or of an essentially similar sequence comprising at least 85%, 90%, 95%, 98%, 99% sequence identity to SEQ ID NO:1 (or to SEQ ID NO: 9) (referred to as SNP marker mME15090) and/or they comprise at least a Adenine (A) (i.e. the AA or AG genotype) instead of two Guanines (GG) at nucleotide 71 of SEQ ID NO: 3 (or SEQ ID NO: 10) or of an essentially similar sequence comprising at least 85%, 90%, 95%, 98%, 99% sequence identity to SEQ ID NO:3 (or to SEQ ID NO: 10) (referred to as SNP marker mME12135). The SNP genotype refers to two nucleotides, and genomic sequences comprising one of these two nucleotides, one on each chromosome 6. So a plant having a CC genotype for mME15090 has an identical nucleotide (C) on both chromosomes, while a plant having an AC genotype for mME15090 has one chromosome with an A at nucleotide 71 of SEQ ID NO: 1 and one chromosome with a C at nucleotide 71 of SEQ ID NO: 1. The "resistant SNP genotype" refers to the genotype of the plant or plant part for the SNP maker whereby the SNP genotype is indicative of presence of the resistance (and introgression fragment comprising the resistance allele), so e.g. the resistant SNP genotype for SNP marker mME15090 is CC (homozygous) or AC (heterozygous).

In a further embodiment, the introgression fragment, or the chromosome 6 region (or orthologous chromosome 6 region) comprising the MYaV-resistance locus, is detectable by a molecular marker assay which further detects at least one, two, three, four, five, six, seven or all eight of the Single Nucleotide Polymorphism (SNP) markers selected from the group consisting of:

a) the GG or AG genotype for the SNP marker mME40332 in SEQ ID NO: 2, or in a sequence comprising at least 85%, 90%, 95%, 98%, 99% sequence identity to SEQ ID NO:2;
b) the TT or AT genotype for the SNP marker mME28908 in SEQ ID NO: 4 or in a sequence comprising at least 85%, 90%, 95%, 98%, 99% sequence identity to SEQ ID NO:4;
c) the AA or AT genotype for the SNP marker mME9692 in SEQ ID NO: 6 or in a sequence comprising at least 85%, 90%, 95%, 98%, 99% sequence identity to SEQ ID NO:6;
d) the CC or CT genotype for the SNP marker mME50656 in SEQ ID NO: 7 or in a sequence comprising at least 85%, 90%, 95%, 98%, 99% sequence identity to SEQ ID NO:7;
e) the AA or AG genotype for the SNP marker mME21377 in SEQ ID NO: 8 or in a sequence comprising at least 85%, 90%, 95%, 98%, 99% sequence identity to SEQ ID NO:8;
f) the TT or GT genotype for the SNP marker mME36533 in SEQ ID NO: 11 or in a sequence comprising at least 85%, 90%, 95%, 98%, 99% sequence identity to SEQ ID NO:11;
g) the TT or CT genotype for the SNP marker mME13585 in SEQ ID NO: 12 or in a sequence comprising at least 85%, 90%, 95%, 98%, 99% sequence identity to SEQ ID NO:12.

Thus, in one aspect the MYaV-resistant melon plant according to the invention further comprises at least a Guanine (G) (i.e. the GG or AG genotype) instead of two Adenines (AA) at nucleotide 71 of SEQ ID NO: 2 or a sequence comprising at least 85%, 90%, 95%, 98%, 99% sequence identity to SEQ ID NO:2 (referred to as SNP marker mME40332), and/or at least a Thymine (T) (i.e. the TT or AT genotype) instead of two Adenines (AA) at nucleotide 71 of SEQ ID NO: 4 or in a sequence comprising at least 85%, 90%, 95%, 98%, 99% sequence identity to SEQ ID NO:4 (referred to as SNP marker mME28908), and/or at least an Adenine (A) i.e. the AA or AT genotype) instead of two Thymines (TT) at nucleotide 71 of SEQ ID NO: 6 or in a sequence comprising at least 85%, 90%, 95%, 98%, 99% sequence identity to SEQ ID NO:6 (referred to as SNP marker mME9692), and/or at least a Cytosine (C) (i.e. the CC or CT genotype) instead of two Thymines (TT) at nucleotide 71 of SEQ ID NO: 7 or in a sequence comprising at least 85%, 90%, 95%, 98%, 99% sequence identity to SEQ ID NO:7 (referred to as SNP marker mME50656), and/or at least a Adenine (A) i.e. the AA or AG genotype) instead of two Guanines (GG) at nucleotide 71 of SEQ ID NO: 8 or in a sequence comprising at least 85%, 90%, 95%, 98%, 99% sequence identity to SEQ ID NO:8 (referred to as SNP marker mME21377), and/or at least a Thymine (T) (i.e. the TT or GT genotype) instead of two Guanines (GG) at nucleotide 71 of SEQ ID NO: 11 or in a sequence comprising at least 85%, 90%, 95%, 98%, 99% sequence identity to SEQ ID NO:11 (referred to as SNP marker mME36533), and/or at least a Thymine (T) (i.e. the TT or CT genotype) instead of two Cytosines (CC) at nucleotide 71 of SEQ ID NO: 12 or in a sequence comprising at least 85%, 90%, 95%, 98%, 99% sequence identity to SEQ ID NO:12 (referred to as SNP marker mME13585).

In one aspect, the introgression fragment, or the chromosome 6 region (or orthologous chromosome 6 region) comprising the MYaV-resistance locus, which is detectable by the above one or more markers is from a wild plant of the species Cucumis melo, and in one aspect it is from a plant of which a representative sample of seeds has been deposited under accession number NCIMB 41966, NCIMB 41969, NCIMB41967 or NCIMB 41968, thus the QTL, and the chromosome 6 region comprising the QTL, is in one aspect the QTL as found in NCIMB 41966 or in NCIMB 41969 or in NCIMB41967 or in NCIMB41968. In one aspect the introgression fragment, or the recombinant chromosome 6, is obtained from crossing a plant grown from seeds deposited under accession number NCIMB 41966 or NCIMB 41969 or NCIMB 41967 or NCIMB41968 with another melon plant, especially a cultivated melon plant of the species C. melo.

Thus, in one aspect the MYaV-resistant melon plant according to the invention comprises an introgression fragment on chromosome 6, which is obtainable from seeds of which a representative sample has been deposited under NCIMB 41966 and wherein said introgression fragment comprises at least one, preferably at least two, optionally at least 3, 4, 5, 6 or 7, SNP markers selected from the group consisting of:
a) the CC or AC genotype for the SNP marker mME15090 in SEQ ID NO: 1;
b) the GG or AG genotype for the SNP marker mME40332 in SEQ ID NO: 2;
c) the AA or AG genotype for the SNP marker mME12135 in SEQ ID NO: 3.
d) the TT or AT genotype for the SNP marker mME28908 in SEQ ID NO: 4;
e) the AA or AT genotype for the SNP marker mME9692 in SEQ ID NO: 6;
f) the CC or CT genotype for the SNP marker mME50656 in SEQ ID NO: 7.

Preferably said at least one marker is selected from mME21377 and/or mME15090.

In another aspect the MYaV-resistant melon plant according to the invention comprises an introgression fragment on chromosome 6, which is obtainable from seeds of which a representative sample has been deposited under NCIMB 41969 and wherein said introgression fragment comprises at least one, preferably at least two, optionally at least 3, 4 or 5 SNP markers selected from the group consisting of:
a) the AA or AG genotype for the SNP marker mME21377 in SEQ ID NO: 8;
b) the CC or AC genotype for the SNP marker mME15090 in SEQ ID NO: 9;
c) the AA or AG genotype for the SNP marker mME12135 in SEQ ID NO: 10;
d) the TT or GT genotype for the SNP marker mME36533 in SEQ ID NO: 11;
e) the TT or CT genotype for the SNP marker mME13585 in SEQ ID NO: 12.

Preferably said at least one marker is selected from mME21377 and/or mME15090.

In still another aspect the MYaV-resistant melon plant according to the invention comprises an introgression fragment on chromosome 6, which is obtainable from seeds of which a representative sample has been deposited under NCIMB 41968 and/or NCIMB 41967, and wherein said introgression fragment comprises at least one, preferably at least two, optionally at least 3 or 4 SNP markers selected from the group consisting of:
a) the AA or AG genotype for the SNP marker mME21377 in SEQ ID NO: 8;
b) the CC or AC genotype for the SNP marker mME15090 in SEQ ID NO: 9;
c) the AA or AG genotype for the SNP marker mME12135 in SEQ ID NO: 10;
d) the TT or CT genotype for the SNP marker mME13585 in SEQ ID NO: 12.

Preferably said at least one marker is selected from mME21377 and/or mME15090.

In one aspect the introgression fragment on chromosome 6, which is obtainable from seeds of which a representative sample has been deposited under NCIMB 41968 or NCIMB41967, does not comprise the TT or GT genotype for the SNP marker mME36533 in SEQ ID NO: 11. In a further aspect the introgression fragment does also further not comprise at least one SNP marker selected from the group consisting of:
the GG or AG genotype for the SNP marker mME40332 in SEQ ID NO: 2;
the TT or AT genotype for the SNP marker mME28908 in SEQ ID NO: 4;
the AA or AT genotype for the SNP marker mME9692 in SEQ ID NO: 6; and
the CC or CT genotype for the SNP marker mME50656 in SEQ ID NO: 7.

To obtain the introgression fragment from the deposited seeds, a plant is grown from the seed and the plant is crossed with a susceptible C. melo plant to obtain F1 seeds. The F1 hybrid seed and plants grown therefrom, contain one chromosome 6 from the susceptible parent (without QTL MYaV6.1) and one chromosome 6 from the wild MYaV-resistant parent. To generate recombination events between these two homologous chromosomes 6, meiosis needs to take place and plants comprising the recombinant chromosomes 6 need to be identified. For example, the F1 can be selfed to produce F2 plants, and/or resistant F2 plants or F3 plants, etc., can be backcrossed to the susceptible parent.

Plants which are resistant to MYaV can be screened for, and selected for, the presence of one or more of the above SNP markers in order to identify plants comprising a recombinant chromosome 6, comprising a MYaV resistance conferring introgression fragment from the deposited seeds.

Similarly, cultivated melon plants comprising resistance against MYaV, whereby the resistance is conferred by an introgression fragment on chromosome 6, can be generated and/or identified using different methods. For example, to obtain a cultivated melon plant comprising a MYaV-resistance conferring introgression fragment from a wild melon or wild relative of melon, first a wild melon or wild relative of melon is identified which has an MYaV resistance phenotype and/or which comprises one or more of the SNP markers associated with MYaV-resistance disclosed herein, e.g. any one, or more, or all of the markers above. Especially markers mME12135 and mME15090, or any marker in between these two, or within 7 cM or within 5 cM of either of these markers, may be used (but also other markers linked to the QTL may be used). The identified plant is crossed with a susceptible C. melo plant to obtain F1 seeds. The F1 hybrid seed and plants grown therefrom, contain one chromosome 6 from the susceptible parent (without QTL MYaV6.1) and one chromosome 6 from the wild MYaV-resistant parent. To generate recombination events between these two homologous chromosomes 6, meiosis needs to take place and plants comprising the recombinant chromosomes 6 need to be identified. For example, the F1 can be selfed to produce F2 plants, and/or resistant F2 plants or F3 plants, etc., can be backcrossed to the susceptible parent. Plants which are resistant to MYaV can be screened for, and/or selected for, the presence of one or more of the above SNP markers and/or screened for, and/or selected for, the presence of the MYaV-resistance phenotype, in order to identify plants comprising a recombinant chromosome 6, comprising a MYaV resistance conferring introgression fragment from the wild melon or wild relative of melon. Alternatively or in addition, QTL mapping can be carried out in order to identify further molecular markers linked to the QTL MYaV6.1 and/or to generate cultivated C. melo plants comprising an introgression fragment on chromosome 6 which confers MYaV-resistance.

In one embodiment the presence of the introgression fragment in a cultivated melon plant, or the chromosome 6 region (or orthologous chromosome 6 region), comprising the MYaV resistance locus, is detectable by a molecular marker assay which detects at least one of the markers selected from the group consisting of:
a) the CC or AC genotype for the SNP marker mME15090 in SEQ ID NO: 1 (or SEQ ID NO: 9) or in a sequence comprising at least 85%, 90%, 95%, 98%, 99% sequence identity to SEQ ID NO: 1;
b) the AA or AG genotype for the SNP marker mME12135 in SEQ ID NO: 3 (or SEQ ID NO: 10) or in a sequence comprising at least 85%, 90%, 95%, 98%, 99% sequence identity to SEQ ID NO:3;
c) any wild melon or wild-relative of melon genome-specific marker in between the markers of a) and b);
d) any wild melon or wild-relative of melon genome-specific marker which genetically linked within 7 cM of marker mME15090 or mME12135; and
e) any wild melon or wild-relative of melon genome-specific marker which is physically linked within 5 Mb, 3 Mb, 2 Mb or 1 Mb of marker mME15090 or mME12135;

In one aspect, at least one, two, at least three, at least four or more markers are detected from the markers of a), b) or c) above. In another aspect, at least one, two, at least three, at least four or more markers are detected from the markers of a), b), c), d) or e) above. In one embodiment at least the marker of a) and/or b) is detected and optionally at least one, two, three or more markers of c), d) and/or e) are detected.

Any wild melon or wild-relative of melon genome-specific marker in between the marker of a) and b) refers to any molecular marker which maps genetically to the chromosome 6 region in-between marker mME15090 and mME12135 (see FIG. 1) and/or which lies physically in-between marker mME15090 and mME12135, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, DNA sequencing, etc. may equally be used.

In another embodiment the presence of the introgression fragment, or the chromosome 6 region (or orthologous chromosome 6 region), comprising the MYaV resistance locus, is detectable by a molecular marker assay which detects at least one of the markers selected from the group consisting of:
a) the CC or AC genotype for the SNP marker mME15090 in SEQ ID NO: 1 (or SEQ ID NO: 9) or in a sequence comprising at least 85%, 90%, 95%, 98%, 99% sequence identity to SEQ ID NO:1;
b) the CC or CT genotype for the SNP marker mME50656 in SEQ ID NO: 7 or in a sequence comprising at least 85%, 90%, 95%, 98%, 99% sequence identity to SEQ ID NO:7; and
c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME15090 and mME50656 (see FIG. 1) and/or which lies physically in-between marker mME15090 and mME50656, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, DNA sequencing, etc. may equally be used.

In one aspect the markers in between marker mME5090 and mME50656 are one or more markers selected from the group: the GG or AG genotype for the SNP marker mME40332 in SEQ ID NO: 2 or in a sequence comprising at least 85%, 90%, 95%, 98%, 99% sequence identity to SEQ ID NO: 2; the AA or AG genotype for the SNP marker mME12135 in SEQ ID NO: 3 or in a sequence comprising at least 85%, 90%, 95%, 98%, 99% sequence identity to SEQ ID NO: 3; the TT or AT genotype for the SNP marker mME28908 in SEQ ID NO: 4 or in a sequence comprising at least 85%, 90%, 95%, 98%, 99% sequence identity to SEQ ID NO:4; and the AA or AT genotype for the SNP marker mME9692 in SEQ ID NO: 6 or in a sequence comprising at least 85%, 90%, 95%, 98%, 99% sequence identity to SEQ ID NO:6.

In yet another embodiment the presence of the introgression fragment, or the chromosome 6 region (or orthologous chromosome 6 region), comprising the MYaV resistance locus, is detectable by a molecular marker assay which detects at least one of the markers selected from the group consisting of:
a) the AA or AG genotype for the SNP marker mME21377 in SEQ ID NO: 8 or in a sequence comprising at least 85%, 90%, 95%, 98%, 99% sequence identity to SEQ ID NO:8;
b) the TT or CT genotype for the SNP marker mME13585 in SEQ ID NO: 12 or in a sequence comprising at least 85%, 90%, 95%, 98%, 99% sequence identity to SEQ ID NO:12; and
c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME21377 and mME13585 (see FIG. 1) and/or which lies physically in-between marker mME21377 and mME13585, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, CASP markers, DNA sequencing, etc. may equally be used.

In one aspect the markers in between marker mME21377 and mME13585 are one or more markers selected from the group: the CC or AC genotype for the SNP marker mME15090 in SEQ ID NO: 9 or in a sequence comprising at least 85%, 90%, 95%, 98%, 99% sequence identity to SEQ ID NO:9; the AA or AG genotype for the SNP marker mME12135 in SEQ ID NO: 10 or in a sequence comprising at least 85%, 90%, 95%, 98%, 99% sequence identity to SEQ ID NO:10; and the TT or GT genotype for the SNP marker mME36533 in SEQ ID NO: 11 or in a sequence comprising at least 85%, 90%, 95%, 98%, 99% sequence identity to SEQ ID NO:11.

In still another embodiment the presence of the introgression fragment, or the chromosome 6 region (or orthologous chromosome 6 region), comprising the MYaV resistance locus, is detectable by a molecular marker assay which detects at least one of the markers selected from the group consisting of:
a) the AA or AG genotype for the SNP marker mME21377 in SEQ ID NO: 8 or in a sequence comprising at least 85%, 90%, 95%, 98%, 99% sequence identity to SEQ ID NO:8;
b) the AA or AG genotype for the SNP marker mME12135 in SEQ ID NO: 3 or in a sequence comprising at least 85%, 90%, 95%, 98%, 99% sequence identity to SEQ ID NO:3; and
c) any wild melon or wild-relative of melon genome-specific marker in between the marker of a) and b).

In one aspect, at least two, at least three, at least four or more markers are detected from the markers of a), b) or c) above. In one embodiment at least the marker of a) and b) is detected and optionally at least one, two, three or more markers of c) are detected.

Any wild melon or wild-relative of melon genome-specific marker in between the marker of a) and b) refers to any molecular marker which maps genetically to the chromosome 6 region in-between marker mME21377 and mME12135 (see FIG. 1) and/or which lies physically in-between marker mME21377 and mME12135, and which is indicative of the wild melon chromosome 6 region or of the wild-relative of melon chromosome 6 region. This means that the marker is polymorphic between the cultivated melon genome and the wild melon or wild-relative of melon genome. In one aspect, the marker is a Single Nucleotide Polymorphism, but other molecular markers such as RFLP, AFLP, RAPD, CASP markers, DNA sequencing, etc. may equally be used.

Thus, provided are herein, a cultivated *Cucumis melo* plant comprising resistance against Melon Yellowing associated Virus (MYaV) wherein said resistance is conferred by an introgression fragment on chromosome 6 in homozygous or heterozygous form and wherein said introgression fragment is from a wild accession of the species *Cucumis melo*, a representative sample of seeds of said wild accession having been deposited under accession number NCIMB 41967 and NCIMB41968.

The plant above has an average MYaV disease score of at least 3 on a scale of 1 totally yellow leaves to 9=totally green leaves when grown in an MYaV infested area, such as in the field in north-eastern Brazil.

In the plant said introgression fragment is detectable by a molecular marker assay which detects at least one of the markers selected from the group consisting of:
a) the CC or AC genotype for the Single Nucleotide Polymorphism marker mME15090 in SEQ ID NO: 1;
b) the AA or AG genotype for the Single Nucleotide Polymorphism marker mME12135 in SEQ ID NO: 3;
c) any wild melon or wild-relative of melon genome-specific marker in between marker mME15090 and mME12135;
d) any wild melon or wild-relative of melon genome-specific marker within 7 cM of mME15090 or mME12135; and
e) any wild melon or wild-relative of melon genome-specific marker within 5 Mb, 3 Mb, 2 Mb or 1 Mb or less of mME15090 or mME12135.

In another aspect, in the plant said introgression fragment is detectable by a molecular marker assay which detects at least one of the markers selected from the group consisting of:
a) the CC or AC genotype for the Single Nucleotide Polymorphism marker mME15090 in SEQ ID NO: 1;
b) the AA or AG genotype for the Single Nucleotide Polymorphism marker mME12135 in SEQ ID NO: 3;
c) the AA or AG genotype for the Single Nucleotide Polymorphism marker mME21377 in SEQ ID NO: 8; and
d) the TT or CT genotype for the Single Nucleotide Polymorphism marker mME13585 in SEQ ID NO: 12.

In a specific aspect of the invention said introgression fragment is detectable in the plant by a molecular marker assay which detects at least one of the Single Nucleotide Polymorphism (SNP) markers selected from the group consisting of:
a) the CC or AC genotype for the Single Nucleotide Polymorphism marker mME15090 in SEQ ID NO: 1; and
b) the AA or AG genotype for the Single Nucleotide Polymorphism marker mME12135 in SEQ ID NO: 3;

In one aspect the plant according to the invention does not comprise the following Single Nucleotide Polymorphism (SNP) markers:
a) the TT or GT genotype for the SNP marker mME36533 in SEQ ID NO: 11; and
b) at least one marker selected from the group consisting of:
   the GG or AG genotype for the SNP marker mME40332 in SEQ ID NO: 2;
   the TT or AT genotype for the SNP marker mME28908 in SEQ ID NO: 4;
   the AA or AT genotype for the SNP marker mME9692 in SEQ ID NO: 6; and
   the CC or CT genotype for the SNP marker mME50656 in SEQ ID NO: 7.

The introgression fragment in the plants of the invention is in one aspect a fragment of the chromosome 6 which is present in seeds deposited under accession number NCIMB41967 or NCIMB41968.

The plant may be an F1 hybrid.

The introgression fragment is in one aspect equal to or less than 10 Mb in size, preferably equal to or less than 8 Mb in size.

Also provided are seeds from which a plant of the invention can be grown, as are melon fruit harvested from a plant of the invention and comprising the recombinant chromosome 6 in their genome. Likewise a plant cell, tissue or plant part of a plant or of a seed is provided comprising at least one recombinant chromosome 6, wherein said recombinant chromosome 6 comprises an introgression fragment from a wild C. melo plant and wherein said introgression fragment comprises an allele conferring MYaV resistance.

The molecular markers described herein may be detected according to standard method. For example SNP markers can easily be detected using a KASP-assay (see www.kp-bioscience.co.uk) or other assays. A KASP-assay has been developed for a number of SNPs in Example 3. For developing the KASP-assay 70 base pairs upstream and 70 base pairs downstream of the SNP were selected and two allele-specific forward primers and one allele specific reverse primer was designed. See e.g. Allen et al. 2011, Plant Biotechnology J. 9, 1086-1099, especially p 097-1098 for KASP assay method.

Thus, in one aspect, the SNP markers and the presence/absence of the marker associated with the MYaV-resistance allele is determined using a KASP assay, but equally other assays can be used. For example, optionally DNA sequencing may also be used.

Physical mapping using BACs (Bacterial Artificial Chromosomes) and development of markers for the BACs can be carried out to map the physical location of MYaV6.1 on chromosome 6 and to develop markers which lie physically between any of the markers mentioned and to determine physical distances between markers and/or determine introgression size.

The size of an introgression fragment can for example also be determined by visualization of the introgression using Fluorescent in situ hybridization (FISH) images (Verlaan et al. 2011, Plant Journal 68: 1093-1103).

In one embodiment of the invention, the MYaV-resistance conferring introgression fragment is equal to or less than 10 Mb in size, preferably equal to or less than 8 Mb in size, equal to or less than 7, 6, 5, 4, 3, 2 or 1 Mb in size, more preferably even less, such as equal to or less than 500 kb, 400 kb, 300 kb, 200 kb, 100 kb, 50 kb, 25 kb, 20 kb, 15 kb, or less, but still comprises the MYaV-resistance allele (or ortholog) and still confers MYaV resistance to an otherwise susceptible C. melo plant. Resistance is conferred by the recombinant chromosome 6, and the introgression fragment comprising the MYaV allele when the introgression fragment is in heterozygous or homozygous form. Plants with smaller introgression fragments on chromosome 6 can be generated by generating new recombinant plants from a population of plants derived from a cross between a cultivated MYaV susceptible plant and a wild MYaV resistant melon or relative of melon. Alternatively, when a cultivated C. melo plant having a MYaV-resistance conferring introgression fragment is identified, the introgression size can be reduced by e.g. selfing that plant and selecting recombinant progeny having smaller introgression sizes.

In tomato, for example the large S. chilense introgression fragment on chromosome 6 (about 27 cM) which comprises the Ty-3 allele has been reduced by selecting a recombinant progeny line (LA1931-AL-F2), which comprises a much smaller S. chilense introgression fragment (about 6 cM) comprising Ty-3 (see Ji et al. 2007, Mol. Breeding 20: 271-284).

The cultivated melon plant according to the invention may be an inbred line, an OP (open pollinated variety) or an F1 hybrid. In one aspect the F1 hybrid comprises the introgression fragment in heterozygous form, i.e. produced by crossing two inbred parent lines, one of which possesses the introgression fragment (preferably in homozygous form, although not necessarily) and collecting the F1 hybrid seeds from said cross. The F1 hybrid may also comprise the introgression fragment in homozygous form, i.e. produced by crossing two inbred parent lines, each comprising the introgression fragment in homozygous or heterozygous form.

The cultivated melon plant may be of any type. Preferably it has good agronomic and good fruit quality characteristics, such as large average fruit size (at least 500 g, 600 g, 700 g, 800 g, 900 g, 1000 g or more), high average brix of the fruits (e.g. an average refractometer % total soluble solids of at least 10%, 12%, 14%, 16%, 18% or more), many fruits being produced per plant, firm fruit flesh, etc. The cultivated melon may be a C. melo cantalupensis, C. melo inodorous and C. melo reticulatus. C. melo cantalupensis are also referred to as Cantaloupes and are primarily round in shape with prominent ribs and almost no netting. Most have orange, sweet flesh and they are usually very fragrant. In contrast to the European cantaloupe, the North American 'Cantaloupe' is not of this type, but belongs to the true muskmelons. C. melo inodorous (or winter melons) can be subdivided into different types, such as Honeydew melon, Piel de Sapo, Sugar melon, Japanese melon, etc. C. melo reticulatus is the true muskmelon, with reticulated skin (netted) and includes Galia melons, Sharlyn melons and the North American cantaloupe. Melons come in many sizes and shapes including round, oval, and cylindrical. The flesh is generally orange and quite sweet, but some varieties of melon and specifically, the Persian melons, can have green or white flesh. Some green-fleshed melons are quite sweet, but most of the green- and white-fleshed melons have a less sweet, but very refreshing flavor.

Also other resistances may be introduced into the melon plants of the invention, such as resistance to one or more of the following diseases: Bacterial Wilt, Root Rot, Crown Blight, Melon Rust, Powdery Mildew, Verticillum Wilt, Sulphur Burn, Scab, Watermelon Mosaic, Downy Mildew, Fusarium oxysporum f. sp. melonis (Fom) race 0, Fusarium oxysporum f. sp. melonis (Fom) race 1, Fusarium oxysporum f. sp. melonis (Fom) race 2, Fusarium oxysporum f. sp. melonis (Fom) race 1.2, Fusarium Wilt R2, Root Knot (Nematode), Anthracnose, Cucumber Mosiac, and Squash Mosaic, and/or resistance to one or more of the following pests: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

In one aspect seeds from which plants of the invention can be grown are provided. In one aspect the seeds are F1 hybrid seeds, which comprise the recombinant chromosome 6 in homozygous or heterozygous form and which have an MYaV-resistance phenotype when grown in the field.

Also containers and packages containing or comprising seeds from which plants of the invention can be grown are provided herein. These may be labelled as containing cultivated melon seeds having MYaV resistance.

Also progeny seeds and progeny plants of plants of the invention are provided, which retain the MYaV resistance conferring introgression on chromosome 6, or a smaller introgression, i.e. a resistance conferring part of the introgression fragment. Progeny may be any generation obtained by selfing a melon plant according to the invention and/or crossing a melon plant according to the invention with another melon plant one or more times. Progeny are, therefore, either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or 51 and/or BC1 generation (or plants of any further generation, e.g. the F2) with another melon plant (and/or with a wild relative of melon). Progeny are preferably selected to retain the recombinant chromosome 6 comprising the introgression fragment from wild melon or from a wild relative of melon. Thus progeny also have the MYaV-resistance phenotype, preferably the same level of MYaV resistance as the plant used in the initial cross or selfing. The presence of (or retention of) the introgression fragment comprising the QTL MYaV6.1 can be determined in the MYaV-resistance assay, phenotypically, and/or the molecular marker assay(s) described herein. Regarding phenotypic assessment, of course consideration needs to be given to the dominance nature of the MYaV-allele.

In a further aspect parts of the melon plants according to the invention are provided. Parts include for example cells and cell-cultures, tissue cultures, vegetative plant tissues (leaves, roots, etc.), flowers, pollen, embryos, fruits, parts of fruits, etc. The plant parts comprise the introgression fragment on chromosome 6, as described, and as can be detected using one or more of the MYaV-marker assays described. Also, when whole plants are regenerated from such melon parts, such as cells, cell- or tissue cultures, the regenerated plants comprise the recombinant chromosome 6, and the MYaV resistance phenotype.

Thus, also provided is a plant cell, tissue or plant part of a plant or of a seed according the invention comprising at least one recombinant chromosome 6, wherein said recombinant chromosome 6 comprises an introgression fragment from a wild C. melo plant and wherein said introgression fragment comprises an allele conferring MYaV resistance.

Also in vitro cell cultures and in vitro tissue cultures are encompassed herein, of cells or tissues comprising a recombinant chromosome 6 described. Preferably the cells or tissues can be regenerated into a whole melon plant, i.e. the cells are regenerable cells and the tissues comprise regenerable cells. Thus, also vegetative propagations of the plants according to the invention are an embodiment herein. Thus, a vegetatively propagated cultivated melon plant is provided which comprises the MYaV resistance phenotype and a recombinant chromosome 6 as described herein.

In a specific aspect a melon fruit harvested from a plant according to the invention is provided. Marketable melon fruits are generally sorted by size and quality after harvest. Also containers or packages comprising or consisting of harvested melon fruits are provided. Again, the cells of the fruits are distinguishable from other melons by the presence of the recombinant chromosome 6 (as determinable in one or more of the molecular marker assays and/or in an MYaV-resistance assay by e.g. growing the seeds present in the fruits, or progeny obtained by selfing the plants grown from the seeds).

The invention also provides for a food or feed product comprising or consisting of a plant part described herein preferably a melon fruit or part thereof and/or an extract from a plant part described herein. The food or feed product may be fresh or processed, e.g., canned, steamed, boiled, fried, blanched and/or frozen, etc. For example, containers such as cans, boxes, crates, bags, cartons, Modified Atmosphere Packaging, films (e.g. biodegradable films), etc. comprising plant parts such as fruits or fruit parts (fresh and/or processed) described herein are also provided herein.

Methods and Uses According to the Invention

In a further embodiment, the invention provides for a method of producing a new cultivated melon plant which comprises an introgression fragment which confers MYaV-resistance when in homozygous or heterozygous form, as described. The method comprises crossing a plant of the invention, or a progeny plant thereof, either as male or as female parent, with a second melon plant (or a wild relative of melon) one or more times, and/or selfing a melon plant according to the invention, or a progeny plant thereof, one or more times, and selecting progeny from said crossing and/or selfing. The first and/or the second melon plant may for example be a line or variety of the species *C. melo cantalupensis, C. melo inodorous* or *C. melo reticulatus*.

Thus, a method for transferring the recombinant chromosome 6, comprising the MYaV-resistance conferring locus (MYaV6.1), from one (cultivated) melon plant into another (cultivated) melon plant is provided, especially into MYaV-susceptible varieties or breeding lines.

The method comprises the steps of:
a) providing a first melon plant comprising at least one recombinant chromosome 6 having an introgression fragment comprising an allele conferring MYaV resistance in homozygous form,
b) providing a second melon plant, especially a MYaV susceptible melon plant,
c) crossing said melon plant of a) with said melon plant of b),
d) collecting F1 hybrid seeds from said cross and optionally
e) selfing the plant grown from said F1 hybrid seeds to produce F2 seeds, and optionally selecting the F2 seeds having the recombinant chromosome 6, and optionally
f) breeding further with plants grown from said F2 seeds to produce a melon plant having good agronomic characteristics and comprising the introgression fragment in homozygous or heterozygous form.

The presence or absence of the recombinant chromosome 6, and of the introgression fragment, may be determined by one or more of the molecular marker assays described herein and/or by MYaV-resistance assays. Further breeding in step f) may comprise selfing, crossing, double haploid production, backcrossing, etc. Plants and seeds obtainable by the above method are encompassed herein.

Also provided is a method of producing *C. melo* F1 hybrid plants comprising a MYaV resistance phenotype, said method comprising:
a) providing a first inbred melon plant comprising at least one recombinant chromosome 6 having an introgression fragment comprising an allele conferring MYaV resistance,
b) providing a second inbred melon plant with or without recombinant chromosome 6 having an introgression fragment comprising an allele conferring MYaV resistance,
c) crossing said melon plant of a) with said melon plant of b),
d) collecting F1 hybrid seeds from said cross.

The inbred melon plant of a) and b) may be homozygous and/or heterozygous for the introgression fragment, and they may contain introgression fragments of different sizes and/or of different origin, i.e. from different wild melons or wild relatives of melon. So, for example the introgression fragment in a) may be the same or a different introgression fragment than in b). For example in a) it may be from any one of the four wild accessions disclosed herein (NCIMB 41966, NCIMB41969, NCIMB41967, NCIMB41968) and in b) it may be from any of the other three accessions disclosed herein or from any other wild source.

The F1 hybrid seeds preferably comprise at least one recombinant chromosome 6 and the F1 plants grown from the seeds are therefore MYaV resistant in their phenotype.

The presence or absence of the recombinant chromosome 6, and of the introgression fragment, may be determined by one or more of the molecular marker assays described herein and/or by MYaV-resistance assays. Plants and seeds obtainable by the above method are encompassed herein.

In a different aspect a method for producing a cultivated *C. melo* plant comprising an introgression fragment on chromosome 6, wherein said introgression fragment comprises an MYaV-resistance allele, is provided, said method comprising the steps:
a) providing a first cultivated melon plant being susceptible to MYaV,
b) providing a second wild melon plant being resistance to MYaV,
c) crossing said melon plant of a) with said melon plant of b),
d) collecting F1 seeds from said cross and backcrossing an F1 plant to the melon plant of a) to produce a backcross (BC1) population, or selfing said F1 plants one or more times to produce an F2 or F3 or higher generation selfing population,
e) optionally backcrossing a plant of d) one or more times to the melon plant of a) to produce a higher generation backcross population, and
f) identifying a F2, F3, or higher generation selfing, or BC1 or higher generation backcross plant which comprises an introgression on chromosome 6, wherein said introgression fragment comprises an MYaV-resistance allele.

When referring to backcross populations in the method, the backcross populations may also be selfed, i.e. BC1S1, BC1S2, BC2S1, BC2S2, or others.

In one or more of steps b) to f) the presence of the MYaV-resistance allele (or the introgression fragment or wild chromosome 6 region comprising the allele) may be tested (and plants may be selected) by carrying out a molecular marker assay as described elsewhere herein, e.g. by determining whether the plant comprises the CC or AC genotype for the SNP marker mME15090 in SEQ ID NO: 1 (or a or in a sequence comprising at least 85%, 90%, 95%, 98%, 99% sequence identity to SEQ ID NO:1) and/or the AA or AG genotype for the SNP marker mME12135 in SEQ ID NO: 3 or in a sequence comprising at least 85%, 90%, 95%, 98%, 99% sequence identity to SEQ ID NO:3 and/or any wild melon or wild-relative of melon genome-specific marker in between the marker mME15090 and mME12135.

Using this method, one can generate and/or select new cultivated melon plants comprising an introgression with QTL MYaV6.1 from a wild source, such as a wild melon or wild relative of melon (such as from NCIMB 41966 or NCIMB 41969 or NCIMB41967 or NCIMB41968, or other wild melons or wild relatives of melon).

In one aspect the method for producing a cultivated *C. melo* plant comprising an introgression fragment on chromosome 6, wherein said introgression fragment comprises an MYaV-resistance allele, comprises the steps:

a) providing a first cultivated melon plant being susceptible to MYaV,
b) providing a second wild melon plant being resistance to MYaV,
c) crossing said melon plant of a) with said melon plant of b),
d) collecting F1 seeds from said cross and backcrossing an F1 plant to the melon plant of a) to produce a backcross (BC1) population, or selfing said F1 plants one or more times to produce an F2 or F3 population,
e) optionally selfing the backcross population to produce e.g. a BC1S1 or BC1S2 population,
f) identifying a F2, F3, BC1 BC1S1, or BC1S2 plant which comprises the CC or AC genotype for the SNP marker mME15090 in SEQ ID NO: 1 or in a sequence comprising at least 85%, 90%, 95%, 98%, 99% sequence identity to SEQ ID NO:1 and/or the AA or AG genotype for the SNP marker mME12135 in SEQ ID NO: 3 or in a sequence comprising at least 85%, 90%, 95%, 98%, 99% sequence identity to SEQ ID NO:3 and/or any wild melon or wild-relative of melon genome-specific marker in between the marker mME15090 and mME12135.

Also provided is a method for identifying a wild melon plant comprising MYaV resistance on chromosome 6, said method comprising:

a) providing a wild melon accession or several wild melon accessions;
b) screening said wild melon accession(s) using a molecular marker assay which detects at least one SNP marker selected from the group consisting of:
   SNP marker mME15090 in SEQ ID NO: 1 and/or SNP marker mME12135 in SEQ ID NO: 3; and
c) identifying and/or selecting a wild melon plant comprising at least the CC or AC genotype for the SNP marker mME15090 in SEQ ID NO: 1 or in a sequence comprising at least 85%, 90%, 95%, 98%, 99% sequence identity to SEQ ID NO:1 and/or the AA or AG genotype for the SNP marker mME12135 in SEQ ID NO: 3 or in a sequence comprising at least 85%, 90%, 95%, 98%, 99% sequence identity to SEQ ID NO:3 and/or any wild melon or wild-relative of melon genome-specific marker in between the marker mME15090 and mME12135; and optionally
d) confirming MYaV resistance in an MYaV resistance assay; and optionally
e) introgressing said MYaV resistance from said wild accession into cultivated melon.

In step c) also other molecular marker tests described elsewhere herein can be used. With this method one can, thus, screen wild melon accessions or wild relatives of melon for the presence of one or more of the markers and, thus, the presence of QTL MYaV6.1 and introgress the resistance-conferring part of these new resistance sources into cultivated, MYaV-susceptible, melon plants. Plants and seeds obtained by this method are also an embodiment of the invention.

In still another aspect a method for identifying a cultivated C. melo plant comprising an introgression fragment on chromosome 6, wherein said introgression fragment comprises an MYaV-resistance allele, is provided, said method comprising:
a) providing a population of recombinant, cultivated C. melo plants (such as an F2, F3, or higher generation selfing, BC1, BC2, BC1S1 or higher generation backcross population),
b) screening said population using a molecular marker assay which detects at least one SNP marker selected from the group consisting of:
   SNP marker mME15090 in SEQ ID NO: 1 or in a sequence comprising at least 85%, 90%, 95%, 98%, 99% sequence identity to SEQ ID NO:1 and/or SNP marker mME12135 in SEQ ID NO: 3 or in a sequence comprising at least 85%, 90%, 95%, 98%, 99% sequence identity to SEQ ID NO: 3 and/or any wild melon or wild-relative of melon genome-specific marker in between the marker mME15090 and mME12135; and
c) identifying and/or selecting a plant comprising at least the CC or AC genotype for the SNP marker mME15090 in SEQ ID NO: 1 or in a sequence comprising at least 85%, 90%, 95%, 98%, 99% sequence identity to SEQ ID NO:1 and/or the AA or AG genotype for the SNP marker mME12135 in SEQ ID NO: 3 or in a sequence comprising at least 85%, 90%, 95%, 98%, 99% sequence identity to SEQ ID NO:3 and/or any wild melon or wild-relative of melon genome-specific marker in between the marker mME15090 and mME12135.

In this method also other molecular marker tests described elsewhere herein can be used. Thus, using this method one can detect the presence of an introgression fragment on chromosome 6 comprising QTL MYaV6.1 in cultivated melon plants or plant parts.

In yet another aspect a method for detecting whether a cultivated C. melo plant comprises an introgression fragment on chromosome 6, wherein said introgression fragment comprises an MYaV-resistance allele, is provided, said method comprising:
a) providing cultivated C. melo plant,
b) screening said plant using a molecular marker assay which detects at least one SNP marker selected from the group consisting of:
   SNP marker mME15090 in SEQ ID NO: 1 or in a sequence comprising at least 85%, 90%, 95%, 98%, 99% sequence identity to SEQ ID NO:1 and/or SNP marker mME12135 in SEQ ID NO: 3 or in a sequence comprising at least 85%, 90%, 95%, 98%, 99% sequence identity to SEQ ID NO:3 and/or any wild melon or wild-relative of melon genome-specific marker in between the marker mME15090 and mME12135.

Molecular marker screening obviously involves obtaining plant material and analyzing the genomic DNA of the material for the marker genotype.

In this method also other molecular marker tests described elsewhere herein can be used. Thus, using this method one can detect the presence of an introgression fragment on chromosome 6 comprising QTL MYaV6.1 in cultivated melon plants or plant parts. If one or more of the markers which are linked to the QTL are present, one can conclude that the plant comprises a MYaV-resistance conferring introgression fragment on chromosome 6.

Also encompassed herein is a method for producing a cultivated C. melo plant comprising an introgression fragment on chromosome 6, wherein said introgression fragment comprises an MYaV-resistance allele, comprising:
a) providing a first cultivated melon plant being susceptible to MYaV,
b) providing a second wild melon plant being resistance to MYaV, selected from plants grown from seeds deposited under accession number NCIMB41967, NCIMB41968 or MYaV-resistant progeny of either of these;
c) crossing said melon plant of a) with said melon plant of b),
d) collecting F1 seeds from said cross and optionally selfing said F1 plants one or more times to produce an F2 or F3 or further selfing population,
e) optionally backcrossing the F1 plant or an F2 or F3 or further selfing plant to the melon plant of a) to produce a backcross population,
f) optionally selfing the backcross population one or more times,
g) identifying a F2, F3, further selfing or backcross plant which comprises the CC or AC genotype for the SNP marker mME15090 in SEQ ID NO: 1 and/or the AA or AG genotype for the SNP marker mME12135 in SEQ ID NO: 3.

In another aspect a method for identifying a cultivated C. melo plant comprising an introgression fragment on chromosome 6 is provided, wherein said introgression fragment comprises an MYaV-resistance allele and wherein said introgression fragment is a fragment of chromosome 6 as found in NCIMB41967 or NCIMB41968, comprising:
a) providing a population of recombinant, cultivated C. melo plants (such as an F2, F3, BC1, BC2, BC1S1 population),
b) screening said population using a molecular marker assay which detects at least one SNP marker selected from the group consisting of:
   SNP marker mME15090 in SEQ ID NO: 1 and SNP marker mME12135 in SEQ ID NO: 3; and
c) identifying and/or selecting a plant comprising at least the CC or AC genotype for the SNP marker mME15090 in SEQ ID NO: 1 and/or the AA or AG genotype for the SNP marker mME12135 in SEQ ID NO: 3.

In a further aspect a method of producing C. melo F1 hybrid plants comprising a MYaV resistance phenotype is provided comprising:
a) providing a first inbred melon plant comprising at least one recombinant chromosome 6 having an introgression fragment comprising an allele conferring MYaV resistance, wherein said introgression fragment is from NCIMB41967, NCIMB41968 or MYaV-resistant progeny of either of these,
b) providing a second inbred melon plant with or without recombinant chromosome 6 having an introgression fragment comprising an allele conferring MYaV resistance,
c) crossing said melon plant of a) with said melon plant of b),
d) collecting F1 hybrid seeds from said cross.

In another aspect a method for generating MYaV resistant progeny of NCIMB41967 or NCIMB41968, said method comprising:

a) growing a plant from seeds deposited under accession number NCIMB41967 or NCIMB41968;
b) selfing said plant one or more times or crossing said plant one or more times with another melon plant to generate progeny seeds;

c) screening said progeny seeds or plants grown from said seeds or parts of the seeds or plants using a molecular marker assay which detects at least one SNP marker selected from the group consisting of:
SNP marker mME15090 in SEQ ID NO: 1 and SNP marker mME12135 in SEQ ID NO: 3; and
d) identifying and/or selecting a progeny plant comprising at least the CC or AC genotype for the SNP marker mME15090 in SEQ ID NO: 1 and/or the AA or AG genotype for the SNP marker mME12135 in SEQ ID NO: 3; and optionally
e) confirming MYaV resistance of the progeny plant in an MYaV resistance assay.

One can also use the methods and the markers described herein to reduce the size of the wild introgression fragment comprising the QTL MYaV6.1, i.e. to generate and select recombinants having a smaller introgression fragment on chromosome 6, but which retain the MYaV resistance conferring part of the introgression fragment. One can equally develop alternative molecular markers linked to MYaV6.1 for use in any of the aforementioned methods.

In one aspect the invention encompasses the use of a recombinant chromosome 6 comprising an introgression fragment from a wild C. melo plant, said introgression fragment comprising an allele conferring MYaV-resistance, for breeding melon varieties having MYaV resistance.

In one aspect the invention encompasses the use of a recombinant chromosome 6 comprising an introgression fragment from a wild C. melo plant, said introgression fragment comprising an allele conferring MYaV-resistance, for breeding melon varieties having MYaV resistance, wherein said recombinant chromosomes 6 is the recombinant chromosome 6 as found in seeds deposited under accession number NCIMB 42113 or NCIMB 42198, or is derived from said recombinant chromosome 6. Thus, in one aspect a cultivated melon plant according to the invention comprising a recombinant chromosome 6 obtained by (obtainable by) crossing a plant grown from seeds deposited under accession number NCIMB 42113 or NCIMB 42198, or from progeny thereof which retain the recombinant chromosome 6, with another melon plant.

Thus, traditional breeding can be used to generate a cultivated melon plant comprising QTL MYaV6.1 from a wild melon or wild relative of melon, which comprises the QTL, as indicative by the presence of the SNP markers, especially at least SNP mME12135 and/or mME15090 in the wild accession and the MYaV-resistance phenotype.

It is noted that at least one of the markers (or two or more) linked to the QTL in the wild accessions are in one aspect also transferred together with the introgression fragment comprising the QTL into the cultivated melon, so that the marker assay on the breeding lines (e.g. backcross populations) and resulting cultivated melon plant can be used to select plants comprising the QTL by selecting plants which have the resistant-genotype of the linked markers, especially SNP mME12135 and/or mME15090.

In one aspect, the plants, cells, tissues and plant parts according to the invention do not comprise the introgression fragment from PI313970, which introgression fragment comprises a CYSDV resistance QTL linked to at least one marker located on the chromosome equivalent to linkage group (LG) 6 of melon accession PI313970 as described and claimed in EP1962578B1. As mentioned, in EP1962578B1 arbitrarily named LG6, but corresponds to ICuGI Linkage Group V (LG V). In one aspect the cultivated melon plants according to the invention comprises a chromosome 5 (ICuGI LG V) and said chromosome 5 does not comprises the introgression from PI313970, which introgression comprises a CYSDV resistance QTL linked to at least one marker located on the chromosome equivalent to linkage group (LG) 6 of melon accession PI313970 as described and claimed in EP1962578B1.

In another aspect, a cultivated melon plant comprising a recombinant chromosome 6 according to the invention and further comprising a recombinant chromosome 5 which comprises an introgression from PI313970, which introgression comprises a CYSDV resistance QTL linked to at least one marker located on the chromosome equivalent to linkage group (LG) 6 of melon accession PI313970 as described and claimed in EP1962578B1 is encompassed herein, i.e. a cultivated melon plant, parts and cells thereof, comprising at least two introgression fragments from wild melon, one conferring MYaV resistance on chromosome 6 (as described throughout the specification) and one conferring CYSDV resistance on chromosome 5 (ICuGI LG V).

Uses are provided herein, such as the use of a recombinant chromosome 6 comprising an introgression fragment from a wild C. melo plant, said introgression fragment comprising an allele conferring MYaV resistance, for breeding melon varieties having MYaV-resistance.

In one aspect, in the use above said recombinant chromosomes 6 is the recombinant chromosome 6 as found in seeds deposited under accession number NCIMB 41967 or NCIMB 41968, or is derived from said recombinant chromosome 6.

Also provided is the use of a chromosome 6 as found in seeds deposited under accession number NCIMB 41967 or NCIMB 41968 or in MYaV-resistant progeny of either of these for generating a MYaV-resistant cultivated melon plant comprising an introgression fragment of said chromosome 6, wherein said introgression fragment confers MYaV resistance.

Also provided is the use of plants grown from seeds deposited under accession number NCIMB 41967 or NCIMB 41968 or MYaV-resistant progeny of either of these, for generating a cultivated melon plant comprising MYaV-resistance, wherein said MYaV-resistance is conferred by an introgression fragment obtained from chromosome 6 of said plants or progeny.

DNA and Chromosomes According to the Invention

In one aspect a modified (recombinant) cultivated C. melo chromosome 6 is provided herein, which comprises an introgression fragment of a wild melon or wild relative of melon, as described throughout the specification. In one aspect the recombinant chromosome 6 is isolated from its natural environment. In another aspect it is in a plant cell, especially in a melon cell, especially in a cultivated C. melo cell. Also an isolated part of the recombinant chromosome 6 comprising the MYaV-allele is provided herein.

In a further aspect a recombinant nucleic acid molecule, especially a recombinant DNA molecule, is provided which comprises a MYaV-allele according to the invention. In one aspect the MYaV-allele is detectable by one or more of the molecular marker assays described herein. Also a DNA vector is provided comprising the recombinant DNA. The recombinant DNA molecule or DNA vector may be an isolated nucleic acid molecule. The DNA comprising the MYaV-allele may be in a microorganisms, such as a bacterium (e.g. *Agrobacterium*).

The use of such a (isolated or extracted) nucleic acid molecule and/or of such a recombinant chromosome 6 or part thereof for generating plant cells and plants (especially melon plant cells and melon plants) comprising a MYaV allele is encompassed herein. In one aspect it may be used to generate transgenic melon cells, melon plants and melon parts (e.g. fruits) comprising the MYaV allele and the plant comprises an MYaV resistance phenotype.

Thus, transgenic plant cells, e.g. transgenic melon cells, comprising in their genome a recombinant chromosome 6 as described and/or a recombinant nucleic acid molecule comprising a MYaV-allele are also an embodiment of the invention. In one aspect the DNA molecule comprising the MYaV-allele is stably integrated into the melon genome.

The MYaV allele may also be cloned and a chimeric gene may be made, e.g. operably linking a plant expressible promoter to the MYaV allele. Such a chimeric gene may be introduced into a plant cell and the plant cell may be regenerated into a whole plant to produce a transgenic plant. In one aspect the transgenic plant is a melon plant.

Thus, transgenic plants, especially transgenic cultivated melon plants, comprising an MYaV resistance allele and having an MYaV resistance phenotype are provided herein.

Especially cells or cell cultures comprising a recombinant chromosome 6 according to the invention are an embodiment, independent whether the recombinant chromosome 6 is introduced by transgenic methods or by breeding methods. The cells are e.g. in vitro and are regenerable into melon plants comprising the recombinant chromosome 6 of the invention.

Also the molecular marker sequences (and isolated nucleic acid molecules comprising the sequence) disclosed herein and molecular markers in between any of the mentioned molecular markers described herein and depicted in FIG. 1, linked to the MYaV-resistance conferring QTL, and their use in detecting and/or generating MYaV resistant melon plants are encompassed herein.

FIGURE LEGENDS

FIG. 1: The LOD profile of MYaV6.1, a QTL on melon linkage group VI (LGVI) conferring resistance to MYaV. The linkage maps of LGVI for the two crosses [(990631-2)-Q-1-K×NCIMB41966 and Amaregal×NCIMB41969] are represented by solid bars, and SNP markers and distances in cM (centiMorgan) are to the right and left sides of the bars, respectively. Common SNP markers between the two maps are indicated with connecting lines. The LOD profile on the (990631-2)-Q-1-K×NCIMB41966 map shows results of field evaluations of replicated F3 families in 2010 while that of Amaregal×NCIMB41969 shows 2011 results of field evaluations of F2 plants. The peak LOD for the cross (990631-2)-Q-1-K×NCIMB41966 was 6.3, explaining 32.6% of observed variation in 2010. The peak LOD of the cross Amaregal×NCIMB41969 was 50.3, explaining 91.7% of observed variation in 2011.

FIG. 2: Photograph taken in Brazil of susceptible melon variety Hibrix (middle row) showing MYaV symptoms. The rectangle shows the part of the melon plant that is phenotyped for symptoms.

SEED DEPOSITS

A representative sample of seeds of wild melon accessions comprising the QTL (designated MYaV6.1) for MYaV resistance on chromosome 6 were deposited by Nunhems B.V. on 2 May 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 41966 and NCIMB 41969 and NCIMB41967 and NCIMB41968.

A representative sample (2600) of seeds (BC1S2) of a cultivated melon plant comprising the QTL for MYaV resistance on chromosome 6 in homozygous form (designated MYaV6.1) was deposited by Nunhems B.V. on 15 Feb. 2013 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit number: NCIMB 42113.

A representative sample of seeds (BC4F2) of a cultivated melon plant comprising the QTL for MYaV resistance on chromosome 6 in homozygous form (designated MYaV6.1) was deposited by Nunhems B.V. on 12 Dec. 2013 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit number: NCIMB 42198.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe how one can obtain plants according to the invention, comprising a recombinant chromosome 6. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard breeding methods are described in 'Principles of Plant breeding', Second Edition, Robert W. Allard (ISBN 0-471-02309-4).

Example 1—Resistance on Chromosome 6 of NCIMB 41966

1.1 Material and Methods

1.1.1 F2 and F3 Population Development

A cross was made between the breeding line (990631-2)-Q-1-K, which is susceptible to MYaV, and a wild melon accession, *Cucmis melo* ssp. *agrestis*, obtained from the USA but originally originating from India, seeds of which were deposited by Nunhems B.V. under accession number NCIMB 41966.

F1 progeny obtained from the cross were selfed to obtain an F2 population, which was used for genotyping (96 F2 plants were genotyped). F2 plants were selfed to obtain F3 families, which were phenotyped in an MYaV resistance assay in the field, near Mossoro, Brazil in 2010, as described below.

1.1.2 MYaV-Resistance Assay of F3 Families

The MYaV-resistance assays were conducted in 2010 in the open field near Mossoro, under natural high MYaV incidence. Each F3 family was planted in three replicates of 20 plants per replicate in 2010, together with susceptible controls (4 plants, 3 replicates) and resistant control NCIMB41966 (20 plants). A complete randomized design was used, as the disease pressure was uniform across the field.

Susceptible controls were Glory F1 (Origene Seeds), Ruidera F1, Amaregal F1, Guapore, Goldex, DRY9150 and Sancho (Syngenta).

Phenotyping for MYaV-symptoms was conducted visually, when the susceptible controls showed clear yellowing symptoms.

Each plant was given a disease score on the following scale, whereby only the older leaves, i.e. the first third (⅓$^{rd}$) of the plant around the main stem and root system, are used. Thus, when referring herein to "all leaves" or "few leaves" or a certain percentage of total leaf area, only the leaves in the oldest ⅓$^{rd}$ of the plant is referred to, see also FIG. 2 where the black rectangle indicates the ⅓$^{rd}$ of the plant that is scored according to the following scale:

| | |
|---|---|
| 9 | Totally green (all leaves in the oldest ⅓$^{rd}$ of the plant are green) |
| 8 | Few leaves (in the oldest ⅓$^{rd}$ of a plant) start to show yellow shadow/mottling |
| 7 | Up to about 17% of total leaf area (in the oldest ⅓$^{rd}$ of a plant) is yellow |
| 6 | About 17% to 32% of total leaf area (in the oldest ⅓$^{rd}$ of a plant) is yellow |
| 5 | 33% to 48% of total leaf area (in the oldest ⅓$^{rd}$ of a plant) is yellow |
| 4 | 49% to 64% of total leaf area (in the oldest ⅓$^{rd}$ of a plant) is yellow |
| 3 | 65% to 80% of total leaf area (in the oldest ⅓$^{rd}$ of a plant) is yellow |
| 2 | 81% to 99% leaves area (in the oldest ⅓$^{rd}$ of the plant) yellow |
| 1 | Totally yellow (all leaves in the oldest ⅓$^{rd}$ of the plant are yellow) |

The average disease score was calculated per F3 family and per control.

1.1.3 Genotyping of F2 Families

Genotyping of F2 families was done using the SNP (Single Nucleotide Polymorphism) Illumina Infinium Array, containing 4600 SNPs. Some ICuGI SSR (Single Sequence Repeat) markers were also analysed and served as anchor markers alongside a few other anchor SNP markers to determine linkage group number and orientation.

1.1.4 Data Analysis of F2 Genotype and F3 Phenotype Data

Linkage mapping was conducted using JoinMap v4 and QTL analysis was conducted with MapQTL v5 software.

1.2 Results 1.2.1 Results of the MYaV Resistance Assay in 2010

The results for the susceptible and resistant checks are shown below:

| | Average Yellowing Scoring |
|---|---|
| MYaV susceptible check varieties | |
| Glory | 2 |
| Ruidera | 1.44 |
| Amaregal | 1.29 |
| Guaporé | 1 |
| Goldex | 1 |
| DRY 9150 | 1 |
| Sancho | 1 |
| MYaV resistant check | |
| NCIMB41966 | 9 |

1.2.2 Results of QTL Mapping of F2 and F3 Families

The SNP markers mapped to 12 linkage groups, corresponding to the haploid chromosome number of melon.

For the 2010 phenotype data a significant QTL for MYaV resistance was found on linkage group VI (based on ICuGI nomenclature), with a peak LOD score of 6.3 and explaining 32.6% of the observed phenotypic variation for MYaV resistance.

The results are shown in FIG. 1.

The following SNP markers were associated with the MYaV resistance phenotype. The SNP genotype of the resistant and susceptible parent at the marker locus is also indicated in the Table.

TABLE 1

| NMID | SNP | Susceptible parent: (990631-2)-Q-1-K | Resistant parent NCIMB 41966 | SNP genotype of resistant heterozygous plant (comprising 1 recombinant chromosome) | LOD score (2010 data) | SEQ ID NO: |
|---|---|---|---|---|---|---|
| mME15090 | [A/C] | AA | CC | CA | 1.33** | 1 |
| mME40332 | [A/G] | AA | GG | GA | 2.20** | 2 |
| mME12135 | [A/G] | GG | AA | AG | 5.30 | 3 |
| mME28908 | [A/T] | AA | TT | TA | 5.26 | 4 |
| mME9692 | [A/T] | TT | AA | AT | 3.13 | 6 |
| mME50656* | [C/T] | TT | CC | CT | 1.43** | 7 |

*corresponds to EST marker A_38-F04 (GenBank Accession AM730270), which was used to link the genetic map of linkage group VI to the physical map (scaffold 00021). See Garcia-Mas et al. June 2012, PNAS Early Edition, page 1-6, Supplementary Information Appendix - FIG. S2.

**even though the LOD score is below 3.0, these markers are still considered significant, as confirmed using separate phenotyping data obtained in 2009 (results not shown)

Example 2—Resistance on Chromosome 6 of NCIMB 41969

2.1 Material and Methods

2.1.1 F2 Population Development

A cross was made between the hybrid Galia melon variety Amaregal F1, which is susceptible to MYaV, and a wild melon accession, obtained from Spain but originally originating from Uzbekistan, seeds of which were deposited by Nunhems B.V. under accession number NCIMB 41969.

F1 progeny obtained from the cross were selfed to obtain an F2 population, which was used for genotyping (181 F2 plants). F2 plants were phenotyped in an MYaV resistance assay in the field, near Mossoro, Brazil in 2011, as described below.

2.1.2 MYaV-Resistance Assay of F2 Plants

The MYaV-resistance assays were conducted in 2011 in the open field near Mossoro, under natural high MYaV incidence.

Susceptible controls (10 plants per plot) were Amaregal (Nunhems), Sancho (Syngenta), and Caribbean Gold. Also NCIMB 41969 was included as resistant check (20 plants per plot).

Phenotyping for MYaV-symptoms was conducted visually, when the susceptible controls showed clear yellowing symptoms.

Each plant was given a disease score on the scale described above under 1.1.2.

The average disease score was calculated per plant line or variety.

2.1.3 Genotyping of F2 Families

Genotyping of F2 plants was done using a genome wide set of 96 markers on a KASP-platform for the initial scaffold map. Some ICuGI SSR (Single Sequence Repeat) markers were also analysed and served as anchor markers alongside a few other anchor SNP markers to determine linkage group number and orientation.

2.1.4 Data Analysis of F2 Genotype and F2 Phenotype Data

Linkage mapping was conducted using JoinMap v4 and QTL analysis was conducted with MapQTL v5 software.

2.2 Results

2.2.1 Results of the MYaV Resistance Assay in 2011

The results for the susceptible and resistant checks are shown below:

|  | Average Yellowing Scoring |
|---|---|
| MYaV susceptible check varieties | |
| Amaregal | 1 |
| Sancho | 1 |
| Caribbean Gold | 1 |
| MYaV resistant check | |
| NCIMB41969 | 9 |

2.2.2 Results of QTL Mapping of F2 Plants

The SNP markers mapped to 12 linkage groups, corresponding to the haploid chromosome number of melon.

A significant QTL for MYaV resistance was found on linkage group VI (based on ICuGI nomenclature), with a peak LOD score of 50.3 and explaining 91.7% of the observed phenotypic variation for MYaV resistance.

The results are shown in FIG. 1.

The following SNP markers were associated with the QTL. The SNP genotype of the resistant and susceptible parent at the marker locus is also indicated in the Table.

TABLE 2

| NMID | SNP | Susceptible parent: | Resistant parent NCIMB 41969 | SNP genotype of resistant heterozygous plant (comprising 1 recombinant chromosome) | LOD score (2011 data) | SEQ ID NO: |
|---|---|---|---|---|---|---|
| mME21377 | [A/G] | GG | AA | AG | 6.81 | 8 |
| mME15090 | [A/C] | AA | CC ( | CA | 17.14 | 9 |
| mME12135 | [A/G] | GG | AA | AG | 24.86 | 10 |
| mME36533 | [G/T] | GG | TT | TG | 7.64 | 11 |
| mME13585 | [C/T] | CC | TT | TC | 6.58 | 12 |

Examples 1 and 2, above, show that an introgression fragment from wild melons, comprising a MYaV resistance conferring locus, confers MYaV-resistance when transferred into cultivated melon. As the QTL mapped to linkage group 6, the QTL was termed MYaV6.1. Seeds of such cultivated melon plants comprising the QTL termed MYaV6.1, have been deposited under deposit number NCIMB 42113 (comprising the introgression fragment from NCIMB 41969) and NCIMB 42198 (comprising the introgression fragment from NCIMB 41966).

The QTL MYaV6.1 was found in two wild melon accessions, from different origins (India and Uzbekistan), and two SNP markers (mME12135 and ME15090) was found to be commonly linked to the QTL in both populations, while four SNP markers (mME40332, mME28908, mME9692 and mME50656) and three SNP markers (mME21377, mME36533 and mME13585) were associated with (linked to) the QTL derived from NCIMB41966 and NCIMB41969, respectively.

One or more (at least two, three, four, five, six, seven, or more) or all of the SNP markers associated with MYaV6.1 provided herein, can be used for various purposes, such as
a) to detect the presence of an introgression fragment on chromosome 6 comprising QTL MYaV6.1 in cultivated melon plants or plant parts;
b) to transfer the recombinant chromosome 6, comprising the MYaV-resistance conferring locus (MYaV6.1), from one cultivated melon into other cultivated melon plants, especially MYaV-susceptible varieties or breeding lines;

c) to generate and/or select new cultivated melon plants comprising an introgression with QTL MYaV6.1 from a wild source, such as a wild melon or wild relative of melon (such as from NCIMB 41966 or NCIMB 41969, or other wild melons or wild relatives of melon), d) to reduce the size of the wild introgression fragment comprising the QTL MYaV6.1, i.e. to generate and select recombinants having a smaller introgression fragment on chromosome 6, but which retain the MYaV resistance conferring part of the introgression fragment;

e) to develop alternative molecular markers for any of the aforementioned purposes, linked to MYaV6.1;

f) to screen wild melon accessions or wild relatives of melon for the presence of one or more of the markers and, thus, the presence of QTL MYaV6.1 and to introgress the resistance-conferring part of these new resistance sources into cultivated, MYaV-susceptible, melon plants.

Example 3—SNP Assays (KASP Assay) or "MYaV-Marker Assay"

In order to screen plants for the presence of one or more of the above molecular markers, linked to the introgression fragment conferring MYaV resistance, a KASP-assay (a SNP genotyping assay or KBioscience Allele-Specific PCR genotyping-assay) was developed for SNP markers mME21377, mME1590, mME12135, mME36533 and mME13585.

Based on the genomic sequences comprising the SNP (see Table 3 below and Sequence listing), for each SNP marker two allele-specific forward primers (i.e. detecting either the nucleotide of the susceptible or resistant parent at the SNP locus) and one common reverse primer (in italics) were developed, indicated in Table 3 and 4 (all sequences are given in 5' to 3' direction).

TABLE 3

| marker | SNP | Genomic sequence for primer design (5' to 3' direction) |
|---|---|---|
| mME12135 | [A/G] | TGCCAGCCGCACGTTTCATCTTTTGGTAATAACTATTAAAAGCAT*AGGAAGCATGTGCTTGAAGGGAGTT*[A/G]GGATCGT AACAAGCGCCACCCTGTTGAATGGAACGGCAATCAGCCTGTCCTTCACCACAAGCATAGTCCA [SEQ ID NO: 3 and SEQ ID NO: 10] |
| mME21377 | [A/G] | TGTATCAGGAACATAGCCAGCTGCTTTCATCTTCTCTG*GCAACGCCTCCAAGAACATGTAGA*TTTCCTTG[A/G]CTTGAG GGTGAGATGTATCGCCACCGAGAAACATATGTGCTTTGCCATTTATCTCGATCCAACTGCAACC [SEQ ID NO: 8] |
| mME15090 | [A/C] | CATTATGATATCTTTCTCTCAACTCAACCATGAACT*CTAAAGCACCATTCCCATCTTTCATCTTT*CGGTA[A/C]GCTCGC AAGGCTGTAGAGTAGGATACGGGAGACAGAGTTAGGCCTTTCTTCGGCATCTCTTCAAGAATGC [SEQ ID NO: 1 and SEQ ID NO: 9] |
| mME36533 | [G/T] | CTATAATACTTCAATAAATAACATGCATACATACATA*CATGGATAATATAGAGAGAAGACAAGGATA*GCT[G/T]AAGTTTA GTAGTTTTGAAGATGTGAATCTCGATTTTTATCTACTACACTGTTTGAATGGAATCCTTTTCT [SEQ ID NO: 11] |
| mME13585 | [C/T] | CATATTATTCTTAAATAATATAAACCACATAATTATTAAA*TTAAATTGAACTAAAACTACCCTATTT TAA*[C/T]GCTTTACAAACTCTTATCTAATGTATGCTTCATTTAATTATTTTTTTGGTTGATACTTTCATTTTATTTT [SEQ ID NO: 12] |

TABLE 4

| marker | SNP | Primer-allele FAM(dye) | Primer-allele VIC(dye) | Probe FAM | Probe VIC | Primer Common |
|---|---|---|---|---|---|---|
| mME12135 | [A/G] | GAAGGTGACCAAGTTCATGCT GGTGGCGCTTGTTACGATCCT (SEQ ID NO: 13) | GAAGGTCGGAGTCAACGGATTG GTGGCGCTTGTTACGATCCC (SEQ ID NO: 14) | T | C | *AGGAAGCATGTGCTTGA AGGGAGTT* (SEQ ID NO: 15) |
| mME21377 | [A/G] | GAAGGTGACCAAGTTCATGCT GGCGATACATCTCACCCTCAA GT (SEQ ID NO: 19) | GAAGGTCGGAGTCAACGGATTGC GATACATCTCACCCTCAAGC (SEQ ID NO: 20) | T | C | *GCAACGCCTCCAAGAAC ATGTAGAT* (SEQ ID NO: 21) |
| mME15090 | [A/C] | GAAGGTGACCAAGTTCATGCT ACTCTACAGCCTTGCGAGCT (SEQ ID NO: 22) | GAAGGTCGGAGTCAACGGATTAC TCTACAGCCTTGCGAGCG (SEQ ID NO: 23) | T | G | *CTAAAGCACCATTCCCAT CTTTCATCTTT* (SEQ ID NO: 24) |
| mME36533 | [G/T] | GAAGGTGACCAAGTTCATGCT AGATTCACATCTTCAAAACTAC TAAACTTC (SEQ ID NO: 25) | GAAGGTCGGAGTCAACGGATTG AGATTCACATCTTCAAAACTACTA AACTTA (SEQ ID NO: 26) | C | A | *CATGGATAATATAGAGA GAAGACAAGGATA* (SEQ ID NO: 27) |
| mME13585 | [C/T] | GAAGGTGACCAAGTTCATGCT GCATACATTAGATAAGAGTTT GTAAAGCG (SEQ ID NO: 28) | GAAGGTCGGAGTCAACGGATTA GCATACATTAGATAAGAGTTTGT AAAGCA (SEQ ID NO: 29) | G | A | *TTAAATTGAACTAAAAC TACCCTATTTTAA* (SEQ ID NO: 30) |

Using the above primers, KASP-assays can be carried out according to standard protocols developed by KBioscience-.co.uk (see www.kbioscience.co.uk), in order to detect the presence of either the resistant or susceptible SNP-genotype in homozygous or heterozygous form in plant DNA derived from melon cells or tissues. If the genotype at a given SNP is homozygous, only one fluorescent signal will be detected. If the genotype of the plant at a given SNP is heterozygous, a mixed fluorescent signal will be detected.

For any of the other SNP markers, e.g. mME40332, mME28908, mME9692 and mME50656, similar SNP-genotyping assays can be developed in order to detect the SNP-genotype.

Example 4—Resistance on Chromosome 6 of NCIMB 41967 and NCIMB 41968

Two other wild accessions of *C. melo*, referred to as *Papaya* netted (NCIMB 41968) and Local 2 (NCIMB 41967), were screened for both MYaV resistance using the same disease assay as described above and for the presence of the SNP markers which are linked to QTL MYaV6.1.

The results are shown below:

| Accessions | Average Yellowing Scoring |
|---|---|
| NCIMB41967 | 9 |
| NCIMB41968 | 9 |
| Amaregal (susceptible) | 1 |

The result of the marker assays are shown below:

| NMID | SNP | Susceptible SNP genotype: | Resistant SNP genotype | Papaya netted - NCIMB41968 | Local 2 - NCIMB41967 |
|---|---|---|---|---|---|
| mME21377 | [A/G] | GG | AA or AG | AA | AA |
| mME15090 | [A/C] | AA | CC or AC | CC | CC |
| mME12135 | [A/G] | GG | AA or AG | AA | AA |
| mME36533 | [G/T] | GG | TT or GT | GG | GG |
| mME13585 | [C/T] | CC | TT or TC | TT | TT |

Thus, both NCIMB41968 and NCIMB41967 comprise the resistance genotype of four markers, including the two common markers. These accession therefore comprises the QTL MYaV6.1 on chromosome 6.

Example 5—Introgression of QTL MYaV6.1 from NCIMB 41967 and NCIMB 41968 into Cultivated Melon Both NCIMB41967 and NCIMB41968 were crossed with the MYaV susceptible cultivar Amaregal (Galia). The F2 population was phenotyped for MYaV resistance and resistant F2 plants (average yellowing score of 9) were backcrossed several times in order to generate a BC4 and BC5 generation comprising the QTL MYaV6.1 on chromosome 6. Marker analysis using the above markers was done to select individuals carrying the resistance genotype of the SNP markers and therefore also the QTL.

The invention claimed is:

1. A non-wild cultivated *Cucumis melo* plant, or part thereof, comprising resistance against Melon Yellowing associated Virus (MYaV) wherein said resistance is conferred by an introgression fragment on chromosome 6 in homozygous or heterozygous form and wherein said introgression fragment is from a wild accession of the species *Cucumis melo*, a representative sample of seeds of said wild accession having been deposited under accession number NCI MB 41967 or NCIMB 41968, wherein said introgression fragment comprises at least two of the following SNP markers:
   a) the CC or AC genotype for the Single Nucleotide Polymorphism marker mME15090 in SEQ ID NO: 1;
   b) the AA or AG genotype for the Single Nucleotide Polymorphism marker mME12135 in SEQ ID NO: 3;
   c) the AA or AG genotype for the Single Nucleotide Polymorphism marker mME21377 in SEQ ID NO: 8; and/or
   d) the TT or CT genotype for the Single Nucleotide Polymorphism marker mME13585 in SEQ ID NO: 12.

2. The plant according to claim 1, wherein said plant has an average MYaV disease score of at least 3 on a scale of 1=totally yellow leaves to 9=totally green leaves when grown in an MYaV infested area.

3. The plant according to claim 1, wherein said introgression fragment comprises at least three of the following SNP markers:
   a) the CC or AC genotype for the Single Nucleotide Polymorphism marker mME15090 in SEQ ID NO: 1;
   b) the AA or AG genotype for the Single Nucleotide Polymorphism marker mME12135 in SEQ ID NO: 3;
   c) the AA or AG genotype for the Single Nucleotide Polymorphism marker mME21377 in SEQ ID NO: 8; and/or
   d) the TT or CT genotype for the Single Nucleotide Polymorphism marker mME13585 in SEQ ID NO: 12.

4. The plant according to claim 1, wherein said introgression fragment comprises at least one of:
   a) the CC or AC genotype for the Single Nucleotide Polymorphism marker mME15090 in SEQ ID NO: 1; and/or
   b) the AA or AG genotype for the Single Nucleotide Polymorphism marker mME12135 in SEQ ID NO: 3.

5. The plant according to claim 1, wherein said plant does not comprise the following Single Nucleotide Polymorphism (SNP) markers:
   a) the TT or GT genotype for the SNP marker mME36533 in SEQ ID NO: 11; and b) at least one of:
      the GG or AG genotype for the SNP marker mME40332 in SEQ ID NO: 2;
      the TT or AT genotype for the SNP marker mME28908 in SEQ ID NO: 4;
      the AA or AT genotype for the SNP marker mME9692 in SEQ ID NO: 6; and/or
      the CC or CT genotype for the SNP marker mME50656 in SEQ ID NO: 7.

6. The plant according to claim 1, wherein said introgression fragment is a fragment of the chromosome 6 which is present in seeds deposited under accession number NCIMB 41967 or NCIMB 41968.

7. The plant according to claim 1, wherein said plant is an F1 hybrid.

8. The plant according to claim 1, wherein said introgression fragment is equal to or less than 10 Mb in size.

9. Seeds from which a plant according to claim 1 can be grown.

10. A melon fruit harvested from a plant according to claim 1.

11. A plant cell, tissue or plant part of a plant or of a seed according to claim 1 comprising at least one recombinant chromosome 6, wherein said recombinant chromosome 6 comprises an introgression fragment from a wild *C. melo* plant and wherein said introgression fragment comprises an allele conferring MYaV resistance.

12. A method for producing a non-wild cultivated *C. melo* plant comprising an introgression fragment on chromosome 6, wherein said introgression fragment comprises an MYaV-resistance allele, comprising:
   a) crossing a first melon plant being susceptible to MYaV with a second melon plant having resistance to MYaV, said second melon plant is grown from seeds deposited under accession number NCI MB 41967, NCI-4IB 41968 or MYaV-resistant progeny of either of these;
   b) collecting F1 seeds from said cross and growing said F1 seeds to obtain F1 plants having an introgression fragment on chromosome 6, wherein said introgression fragment comprises the CC or AC genotype for the SNP marker mME15090 in SEQ ID NO: 1 and/or the AA or AG genotype for the SNP marker mM1E12135 in SEQ ID NO: 3,
   c) optionally selfing said F1 plants one or more times to produce an F2 or F3 or further selfing population,
   d) optionally backcrossing an F1 plant or an F2 or F3 or further selfing plant to the first melon plant of part a) to produce a backcross population, e) optionally selfing the backcross population one or more times, and f) identifying an F2, F3, further selfing or backcross plant which comprises the CC or AC genotype for the SNP marker mM15090 in SEQ ID NO: 1 and/or the AA or AG genotype for the SNP marker mME12135 in SEQ ID NO: 3.

13. A method for identifying a non-wild cultivated *C. melo* plant comprising an introgression fragment on chromosome 6, wherein said introgression fragment comprises an MYaV-resistance allele and wherein said introgression fragment is a fragment of chromosome 6 as found in NCIMB 41967 or NCIM1B 41968 and said introgression fragment comprises the CC or AC genotype for the SNP marker mME15090 in SEQ ID NO: 1 and/or the AA or AG genotype for the SNP marker mME12135 in SEQ ID NO: 3, comprising:

a) screening a population of recombinant, *C. melo* plants using a molecular marker assay which detects at least one of: SNP marker mME15090 in SEQ ID NO: 1 and/or SNP marker mME12135 in SEQ ID NO: 3; and b) identifying and/or selecting a plant comprising at least the CC or AC genotype for the SNP marker mME15090 in SEQ ID NO: 1 and/or the AA or AG genotype for the SNP marker mME12135 in SEQ ID NO: 3.

14. A method of producing *C. melo* F1 hybrid plants comprising a MYaV resistance phenotype comprising:

a) crossing a first inbred melon plant comprising at least one recombinant chromosome 6 having an introgression fragment comprising an allele conferring MYaV resistance, wherein said introgression fragment is from NCIMB 41967, NCIMB 41968 or MYaV-resistant progeny of either of these and said introgression fragment comprises the CC or AC genotype for the SNP marker mME15090 in SEQ ID NO: 1 and/or the AA or AG genotype for the SNP marker mME12135 in SEQ ID NO: 3, with a second inbred melon plant with or without recombinant chromosome 6 having an introgression fragment comprising an allele conferring MYaV resistance, and b collecting F1 hybrid seeds from said cross.

15. A method for generating MYaV resistant progeny of NCIMB41967 or NCIMB41968, said method comprising:

a) growing a plant from seeds deposited under accession number NCIMB41967 or NCIMB41968;

b) selfing said plant one or more times or crossing said plant one or more times with another melon plant to generate progeny seeds;

c) screening said progeny seeds or plants grown from said seeds or parts of the seeds or plants using a molecular marker assay which detects at least one of:

SNP marker mME15090 in SEQ ID NO: 1 and/or SNP marker mME12135 in SEQ ID NO: 3;

d) identifying and/or selecting a progeny plant comprising at least the CC or AC genotype for the SNP marker mME15090 in SEQ ID NO: 1 and/or the AA or AG genotype for the SNP marker mME12135 in SEQ ID NO: 3; and optionally e) confirming MYaV resistance of the progeny plant in an MYaV resistance assay.

16. The plant according to claim 1, wherein said introgression fragment is equal to or less than 8 Mb in size.

* * * * *